US012758341B2

(12) United States Patent
Kadokura

(10) Patent No.: US 12,758,341 B2
(45) Date of Patent: Oct. 13, 2026

(54) CABLE DRIVE LIMITED SLIP CAPSTAN AND SHAFT

(71) Applicant: Intuitive Surgical Operations, Inc., Sunnyvale, CA (US)

(72) Inventor: Grant M. Kadokura, San Diego, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 250 days.

(21) Appl. No.: 18/664,240

(22) Filed: May 14, 2024

(65) Prior Publication Data

US 2024/0366329 A1 Nov. 7, 2024

Related U.S. Application Data

(63) Continuation of application No. 17/293,909, filed as application No. PCT/US2019/061888 on Nov. 15, 2019, now Pat. No. 12,048,504.

(Continued)

(51) Int. Cl.
*A61B 34/00* (2016.01)
*A61B 34/35* (2016.01)
*A61B 34/30* (2016.01)

(52) U.S. Cl.
CPC .............. *A61B 34/71* (2016.02); *A61B 34/35* (2016.02); *A61B 34/76* (2016.02); *A61B 2034/302* (2016.02); *A61B 2034/715* (2016.02)

(58) Field of Classification Search
CPC ......... A61B 34/71; A61B 34/35; A61B 34/76; A61B 2034/302; A61B 2034/715
See application file for complete search history.

(56) References Cited

U.S. PATENT DOCUMENTS 2,091,317 A 8/1937 Hill
2,906,143 A 9/1959 Musser
(Continued)

FOREIGN PATENT DOCUMENTS

CN 101893060 A 11/2010
CN 104799891 A 7/2015
(Continued)

OTHER PUBLICATIONS

International Preliminary Report on Patentability for Application No. PCT/US2019/061888, mailed on May 27, 2021, 10 pages.
(Continued)

*Primary Examiner* — Shirley X Jian

(57) ABSTRACT

Capstan slip-stop shoulders limit relative rotation of capstans: a drive is shaft rotatably inserted within first and second axially aligned annular capstans, the first capstan including a first tooth extending parallel to the drive shaft in a first direction, the second capstan including a second tooth extending parallel to the drive shaft in a second direction opposite the first direction, the first tooth including first and second circumferentially spaced first tooth slip-stop shoulders, the second tooth including first and second circumferentially spaced second tooth slip-stop shoulders, the first and second capstans arranged such that abutting contact between the first and second slip-stop shoulders can halt capstan rotation about the drive shaft in one direction, and abutting contact between the second first and second slip-stop shoulders can halt capstan rotation about the drive shaft in an opposite direction. Halting capstan rotation prevents a cable wrapped around a capstan from paying out and causing misalignment with an end effector controlled by the cable.

20 Claims, 13 Drawing Sheets

Related U.S. Application Data

(60) Provisional application No. 62/767,895, filed on Nov. 15, 2018.

(56) References Cited

U.S. PATENT DOCUMENTS 4,751,821 A 6/1988 Birchard
4,903,536 A 2/1990 Salisbury, Jr. et al.
5,792,135 A 8/1998 Madhani et al.
5,807,377 A 9/1998 Madhani et al.
5,855,583 A 1/1999 Wang et al.
5,876,325 A 3/1999 Mizuno et al.
6,007,550 A 12/1999 Wang et al.
6,817,974 B2 11/2004 Cooper et al.
6,994,708 B2 2/2006 Manzo
7,090,683 B2 8/2006 Brock et al.
7,169,141 B2 1/2007 Brock et al.
7,214,230 B2 5/2007 Brock et al.
7,371,210 B2 5/2008 Brock et al.
7,608,083 B2 10/2009 Lee et al.
7,666,191 B2 2/2010 Orban, III et al.
7,736,254 B2 6/2010 Schena
7,935,130 B2 5/2011 Williams
8,142,421 B2 3/2012 Cooper et al.
8,224,484 B2 7/2012 Swarup et al.
8,444,631 B2 5/2013 Yeung et al.
8,479,969 B2 7/2013 Shelton, IV
8,506,555 B2 8/2013 Ruiz Morales
8,551,115 B2 10/2013 Steger et al.
8,573,465 B2 11/2013 Shelton, IV
8,602,288 B2 12/2013 Shelton, IV et al.
8,771,270 B2 7/2014 Burbank
8,800,838 B2 8/2014 Shelton, IV
8,808,166 B2 8/2014 Hosaka
8,992,565 B2 3/2015 Brisson et al.
9,002,518 B2 4/2015 Manzo et al.
9,028,494 B2 5/2015 Shelton, IV et al.
9,078,684 B2 7/2015 Williams
9,121,494 B2 9/2015 Buchleitner et al.
9,204,923 B2 12/2015 Manzo et al.
9,232,979 B2 1/2016 Parihar et al.
9,259,274 B2 2/2016 Prisco
9,339,342 B2 5/2016 Prisco et al.
9,524,022 B2 12/2016 Nakayama
9,572,616 B2 2/2017 Vaughn
9,664,262 B2 5/2017 Donlon et al.
9,737,373 B2 8/2017 Schuh
9,750,578 B2 9/2017 Alden et al.
9,839,439 B2 12/2017 Cooper et al.
9,931,106 B2 4/2018 Au et al.
9,962,228 B2 5/2018 Schuh et al.
9,993,313 B2 6/2018 Schuh et al.
10,076,348 B2 9/2018 Anderson et al.
10,201,365 B2 2/2019 Boudreaux et al.
10,285,763 B2 5/2019 Vale et al.
10,288,837 B2 5/2019 Miyatani et al.
10,314,583 B2 6/2019 Smith et al.
10,357,321 B2 7/2019 Donlon et al.
10,470,830 B2 11/2019 Hill et al.
10,478,163 B2 11/2019 Prisco et al.
10,478,256 B2 11/2019 Shelton, IV et al.
10,543,051 B2 1/2020 Schena et al.
10,595,948 B2 3/2020 Solomon et al.
10,595,949 B2 3/2020 Donlon et al.
10,624,709 B2 4/2020 Remm
10,772,690 B2 9/2020 Prisco
10,806,530 B2 10/2020 Liao et al.
10,980,556 B2 4/2021 Anderson et al.
11,013,566 B2 5/2021 Diel et al.
11,076,926 B2 8/2021 Ragosta et al.
11,207,145 B2 12/2021 Lambrecht et al.
11,248,686 B2 2/2022 Cooper et al.
11,517,397 B2 12/2022 Lambrecht et al.
12,048,504 B2 * 7/2024 Kadokura .............. A61B 34/71
2002/0111635 A1 8/2002 Jensen et al.
2003/0068607 A1 4/2003 Gregorio et al.
2005/0119527 A1 6/2005 Banik et al.
2006/0190034 A1 8/2006 Nishizawa et al.
2007/0043338 A1 2/2007 Moll et al.
2007/0119274 A1 5/2007 Devengenzo et al.
2007/0232858 A1 10/2007 Macnamara et al.
2008/0009838 A1 1/2008 Schena et al.
2008/0046122 A1 2/2008 Manzo et al.
2008/0103491 A1 5/2008 Omori et al.
2008/0196533 A1 8/2008 Bergamasco et al.
2009/0088774 A1 4/2009 Swarup et al.
2009/0112230 A1 4/2009 Jinno
2009/0148263 A1 6/2009 Lee et al.
2009/0198272 A1 8/2009 Kerver et al.
2010/0011900 A1 1/2010 Burbank et al.
2010/0175701 A1 7/2010 Reis et al.
2010/0198253 A1 8/2010 Jinno et al.
2010/0313706 A1 12/2010 Hellinger et al.
2010/0318101 A1 12/2010 Choi et al.
2011/0015650 A1 1/2011 Choi et al.
2011/0071543 A1 3/2011 Prisco et al.
2011/0118754 A1 5/2011 Dachs, II et al.
2011/0184241 A1 7/2011 Zubiate et al.
2011/0277580 A1 11/2011 Cooper et al.
2011/0277775 A1 11/2011 Holop et al.
2011/0295269 A1 12/2011 Swensgard et al.
2011/0295270 A1 12/2011 Giordano et al.
2011/0313405 A1 12/2011 Anderson et al.
2012/0046522 A1 2/2012 Naito
2012/0109186 A1 5/2012 Parrott et al.
2012/0123441 A1 5/2012 Au et al.
2012/0239060 A1 9/2012 Orban, III et al.
2012/0289974 A1 11/2012 Rogers et al.
2012/0292367 A1 * 11/2012 Morgan ................. A61B 50/36
227/175.1
2013/0046318 A1 2/2013 Radgowski et al.
2014/0005678 A1 1/2014 Shelton, IV et al.
2014/0005708 A1 1/2014 Shelton, IV
2014/0018821 A1 1/2014 Yeung et al.
2014/0100558 A1 4/2014 Schmitz et al.
2014/0107865 A1 4/2014 Shellenberger et al.
2014/0257333 A1 9/2014 Blumenkranz
2014/0276723 A1 9/2014 Parihar et al.
2014/0309625 A1 10/2014 Okamoto et al.
2015/0051034 A1 2/2015 Cooper et al.
2015/0150635 A1 6/2015 Kilroy et al.
2015/0150636 A1 6/2015 Hagn et al.
2015/0157355 A1 6/2015 Price et al.
2016/0058443 A1 3/2016 Yates et al.
2016/0151115 A1 6/2016 Karguth et al.
2016/0296219 A1 10/2016 Srivastava et al.
2016/0361049 A1 12/2016 Dachs, II et al.
2017/0165017 A1 6/2017 Chaplin et al.
2017/0172672 A1 6/2017 Bailey et al.
2017/0207467 A1 7/2017 Shelton, IV et al.
2017/0248194 A1 8/2017 Bae et al.
2017/0265865 A1 9/2017 Burbank
2017/0365239 A1 * 12/2017 Peterson .................. G10D 3/04
2018/0104011 A1 4/2018 Kadokura et al.
2018/0104012 A1 4/2018 Wixey et al.
2018/0126504 A1 * 5/2018 Shelton, IV ........... A61B 90/08
2018/0229021 A1 8/2018 Donlon et al.
2019/0038282 A1 2/2019 Shelton, IV et al.
2019/0099227 A1 4/2019 Rockrohr
2019/0117325 A1 4/2019 Kishi
2019/0125468 A1 5/2019 Adams
2019/0223960 A1 7/2019 Chaplin et al.
2019/0231451 A1 8/2019 Lambrecht et al.
2019/0231464 A1 8/2019 Wixey et al.
2019/0239965 A1 8/2019 Abbott
2019/0249759 A1 8/2019 Abbott
2019/0298323 A1 10/2019 Lambrecht et al.
2019/0328467 A1 10/2019 Waterbury et al.
2020/0008828 A1 1/2020 Overmyer
2020/0093554 A1 3/2020 Schuh et al.
2020/0261168 A1 8/2020 Anglese
2021/0045819 A1 2/2021 Castillo et al.
2021/0093408 A1 4/2021 Carey et al.
2021/0186544 A1 6/2021 Anderson et al.
2021/0220001 A1 7/2021 Heiliger

(56) References Cited

U.S. PATENT DOCUMENTS

| | | | |
|---|---|---|---|
| 2021/0220062 | A1 | 7/2021 | Lambrecht et al. |
| 2021/0282793 | A1 | 9/2021 | Anderson et al. |
| 2021/0322118 | A1 | 10/2021 | Donlon et al. |
| 2021/0372508 | A1 | 12/2021 | Abbott |
| 2021/0401523 | A1 | 12/2021 | Suresh |
| 2021/0401524 | A1 | 12/2021 | Suresh et al. |
| 2022/0015847 | A1 | 1/2022 | Kadokura |
| 2022/0087760 | A1 | 3/2022 | Schuh et al. |
| 2022/0096067 | A1 | 3/2022 | Beckman et al. |
| 2022/0096082 | A1 | 3/2022 | Beckman et al. |
| 2022/0128133 | A1 | 4/2022 | Cooper et al. |
| 2022/0192764 | A1 | 6/2022 | Waterbury et al. |
| 2022/0280253 | A1 | 9/2022 | He et al. |
| 2023/0045998 | A1 | 2/2023 | Shelton, IV et al. |
| 2023/0119001 | A1 | 4/2023 | Abbott |
| 2023/0172680 | A1 | 6/2023 | Reid et al. |
| 2024/0100942 | A1 | 3/2024 | Mattsson et al. |
| 2024/0197423 | A1 | 6/2024 | Ragosta et al. |
| 2024/0315792 | A1 | 9/2024 | Lambrecht et al. |
| 2024/0382279 | A1 | 11/2024 | Baldwin et al. |
| 2025/0000598 | A1 | 1/2025 | Baldwin et al. |
| 2025/0169899 | A1 | 5/2025 | Heye |
| 2025/0186147 | A1 | 6/2025 | Times et al. |
| 2026/0130731 | A1 | 5/2026 | Reid et al. |

FOREIGN PATENT DOCUMENTS

| | | | |
|---|---|---|---|
| CN | 105212987 | A | 1/2016 |
| CN | 109069138 | A | 12/2018 |
| CN | 109505951 | A | 3/2019 |
| CN | 110269686 | A | 9/2019 |
| CN | 110584787 | A | 12/2019 |
| EP | 2362285 | A2 | 8/2011 |
| EP | 2548529 | A1 | 1/2013 |
| EP | 2783643 | A1 | 10/2014 |
| EP | 3103374 | A1 | 12/2016 |
| EP | 3195993 | A1 | 7/2017 |
| EP | 3476321 | A1 | 5/2019 |
| EP | 3508311 | A1 | 7/2019 |
| JP | H06114000 | A | 4/1994 |
| JP | H10249777 | A | 9/1998 |
| JP | 2004301275 | A | 10/2004 |
| JP | 2005288590 | A | 10/2005 |
| WO | WO-8910242 | A1 | 11/1989 |
| WO | WO-9729690 | A1 | 8/1997 |
| WO | WO-2009039506 | A1 | 3/2009 |
| WO | WO-2009079781 | A1 | 7/2009 |
| WO | WO-2012068156 | A2 | 5/2012 |
| WO | WO-2016073637 | A1 | 5/2016 |
| WO | WO-2016161449 | A1 | 10/2016 |
| WO | WO-2016172299 | A1 | 10/2016 |
| WO | WO-2016189284 | A1 | 12/2016 |
| WO | WO-2017064303 | A1 | 4/2017 |
| WO | WO-2017188851 | A1 | 11/2017 |
| WO | WO-2018013313 | A1 | 1/2018 |
| WO | WO-2018069679 | A1 | 4/2018 |
| WO | WO-2018094191 | A1 | 5/2018 |
| WO | WO-2020102780 | A1 | 5/2020 |
| WO | WO-2020252184 | A1 | 12/2020 |
| WO | WO-2021041395 | A1 | 3/2021 |
| WO | WO-2021192255 | A1 | 9/2021 |
| WO | WO-2023055684 | A2 | 4/2023 |

OTHER PUBLICATIONS

International Search Report and Written Opinion for Application No. PCT/US2019/061888 mailed on Mar. 10, 2020, 15 pages.

Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

CABLE DRIVE LIMITED SLIP CAPSTAN AND SHAFT

CROSS-REFERENCE TO RELATED APPLICATIONS

This application is a continuation of U.S. application Ser. No. 17/293,909, entitled "Cable Drive Limited Slip Capstan and Shaft," filed May 13, 2021, which is a U.S. national stage filing under 35 U.S.C. § 371 of International Application No. PCT/US2019/061888, entitled "Cable Drive Limited Slip Capstan and Shaft," filed Nov. 15, 2019, which claims the benefit of priority to U.S. Provisional Patent Application No. 62/767,895, entitled "Cable Drive Limited Slip Capstan and Shaft," filed Nov. 15, 2018, each of which is incorporated herein by reference in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robot assisted technology may be used to overcome limitations of manual laparoscopic and open surgery. Advances in telepresence systems provide surgeons views inside a patient's body, an increased number of degrees of motion of surgical tools, and the ability for surgical collaboration over long distances. In teleoperation surgery systems, a tool operator may actuate an input to a master control device to send control signals to a mechanical control device at a proximal end portion of an elongated tool shaft to control motion of a cable (or a cable-hypotube combination) that extends within a length of the shaft, to control movement of an end effector at a distal end portion of the tool shaft. Thus, direct natural force feedback to a tool operator is largely eliminated because such tool user does not manually manipulate the tool directly.

A force sensor may be disposed at or near a tool shaft to measure clinical forces imparted to patient tissue during a medical procedure due to contact with an end effector, for example. A force sensor often includes a beam having multiple force sensing devices such as strain gauges or fiber Bragg grating optical sensors distributed about its surface. The beam and the tool shaft share a longitudinal axis, referred to as a tool shaft axis. Force measurements at or near a tool shaft may be used to produce haptic feedback forces at an input to a master control device to provide to a user an indication of the forces imparted by the tool to patient tissue, for example. In response to haptic feedback, a user can provide control input to cause a cable drive element to impart motion to a cable to adjust a position of an end effector coupled to the cable.

Rotational orientation of a cable-controlled end effector about the tool shaft axis, referred to as roll position, can depend upon amount of cable played out (i.e. extending) between the cable drive element about which a portion of the cable is wrapped and the end effector to which the cable is operatively coupled. In general, end effector roll position has a known relationship to a rotational position of a cable drive element used to impart motion to cable to adjust end effector position. Based upon the known relationship, a user ordinarily can determine a control input necessary to achieve a desired adjustment of end effector position in response to haptic feedback. Unfortunately, cable slippage at a cable drive element can change the amount of cable played out between the cable drive element and the end effector, which can alter the relationship between end effector roll position and rotational position of the cable drive element. A user who is unaware of the actual changed relationship can mistakenly presume the known relationship, and as a result, provide a control input that adjusts the end effector position differently from what the user intended, in response to the haptic feedback.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
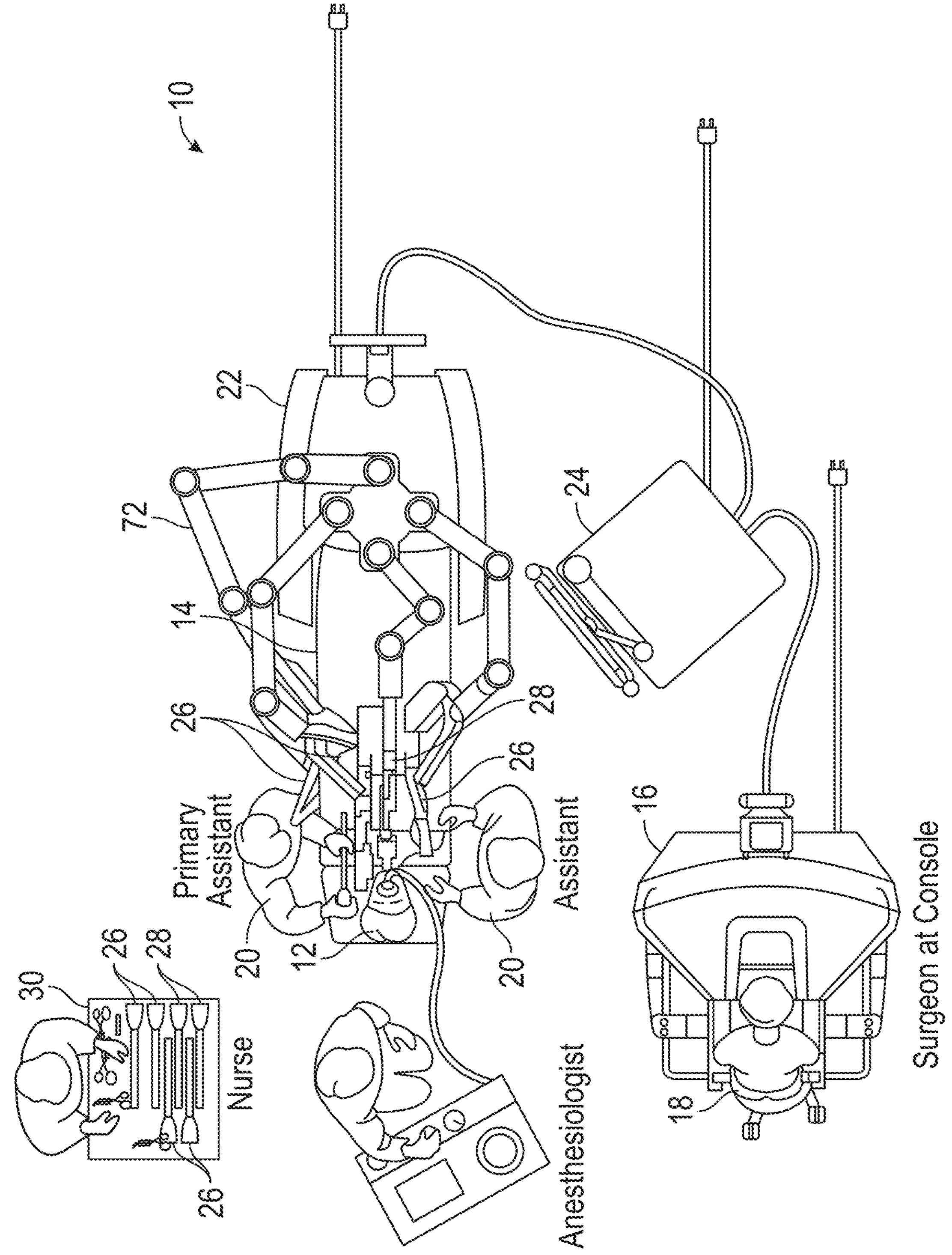
FIG. 1 is an illustrative plan view of a minimally invasive teleoperated surgical system for performing a minimally invasive diagnostic or therapeutic procedures on a patient who is lying on an operating table.

FIG. 1 is an illustrative plan view of a minimally invasive teleoperated surgical system 10 for performing a minimally invasive diagnostic or therapeutic surgical procedure on a patient 12 who is lying on an operating table 14. The system includes a user control unit 16 for use by a surgeon 18 during the procedure. One or more assistants 20 also may participate in the procedure. The minimally invasive teleoperated surgical system 10 further includes one or more manipulator units 22 and an auxiliary unit 24. The manipulator units 22 can manipulate at least one surgical instrument 26 through a minimally invasive incision in the body or a natural body orifice of the patient 12 while the surgeon 18 views the surgical site through the user console 16. An image of the surgical site can be obtained by an endoscope 28, such as a stereoscopic endoscope, which may be positioned using a manipulator unit 22. Computer processors located on the auxiliary unit 24 may be used to process the images of the surgical site for subsequent display to the surgeon 18 through the user console 16. The computer processor can include a logic unit and a memory that stores instructions carried out by the logic unit. In some embodiments, stereoscopic images may be captured, which allow the perception of depth during a surgical procedure. The number of surgical instruments 26 used at one time will generally depend on the diagnostic or therapeutic procedure and the space constraints within the operative site, among other factors. If it is necessary to change one or more of the surgical instruments 26 being used during a procedure, an assistant 20 may remove the surgical instrument 26 from a manipulator unit 22, and replace it with another surgical instrument 26 from a tray 30 in the operating room. An example computer processor at the auxiliary unit 24 can be configured process signals indicative of forces imparted at the surgical instrument. An example computer processor can produce haptic feedback corresponding to these imparted forces at the surgeon's console 16.

Figure 2:
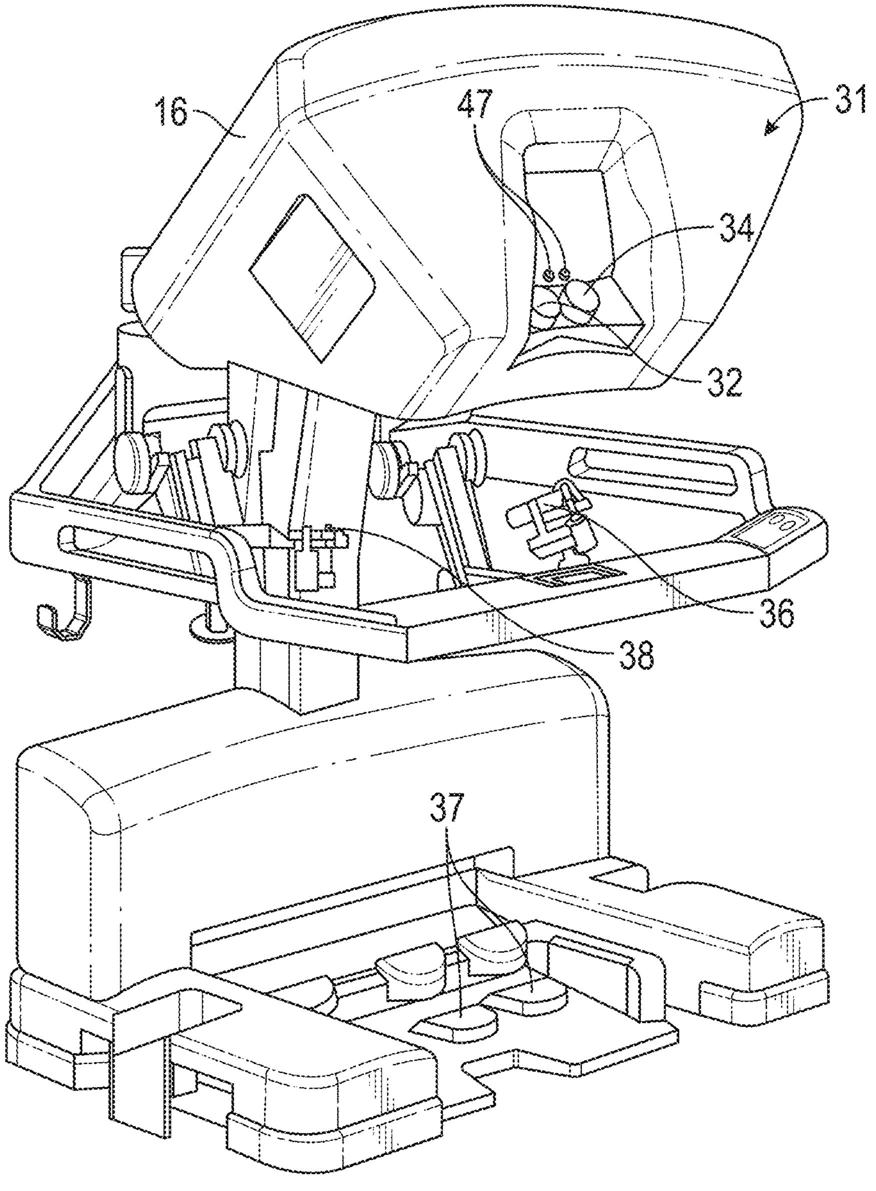
FIG. 2 is a perspective view of a user control unit of a minimally invasive teleoperated surgical system.

FIG. 2 is a perspective view of the user console 16. The surgeon's console 16 includes a viewer display 31 that includes a left eye display 32 and a right eye display 34 for presenting the surgeon 18 with a coordinated stereoscopic view of the surgical site that enables depth perception. The user console 16 further includes one or more hand-operated control input devices 36, 38 to receive larger-scale hand control movements. One or more slave surgical instruments 26 installed for use at on one or more corresponding manipulators manipulator units 22 move in relatively smaller-scale distances that match a surgeon 18's larger-scale manipulation of the one or more master control inputs 36, 38. The master control input devices 36, 38 may provide the same mechanical degrees of freedom as their associated surgical instruments 26 to provide the surgeon 18 with telepresence, or the perception that the master control input devices 36 are integral with the slave surgical instruments 26 so that the surgeon has a keen sense of directly controlling the instruments 26. To this end, position, force, and tactile feedback sensors (not shown) may be employed to transmit position, force, and tactile sensations from the surgical instruments 26 through the control input devices 36,38 to the surgeon's hands, subject to communication delay constraints. Signals (optionally optical or electronic) modulated based upon forces detected at force sensors (not shown) at the instrument 26 may be processed by the processors at the auxiliary unit cart 24 to produce haptic feedback at the control input devices 36 that is indicative of the detected forces.

Figure 3:
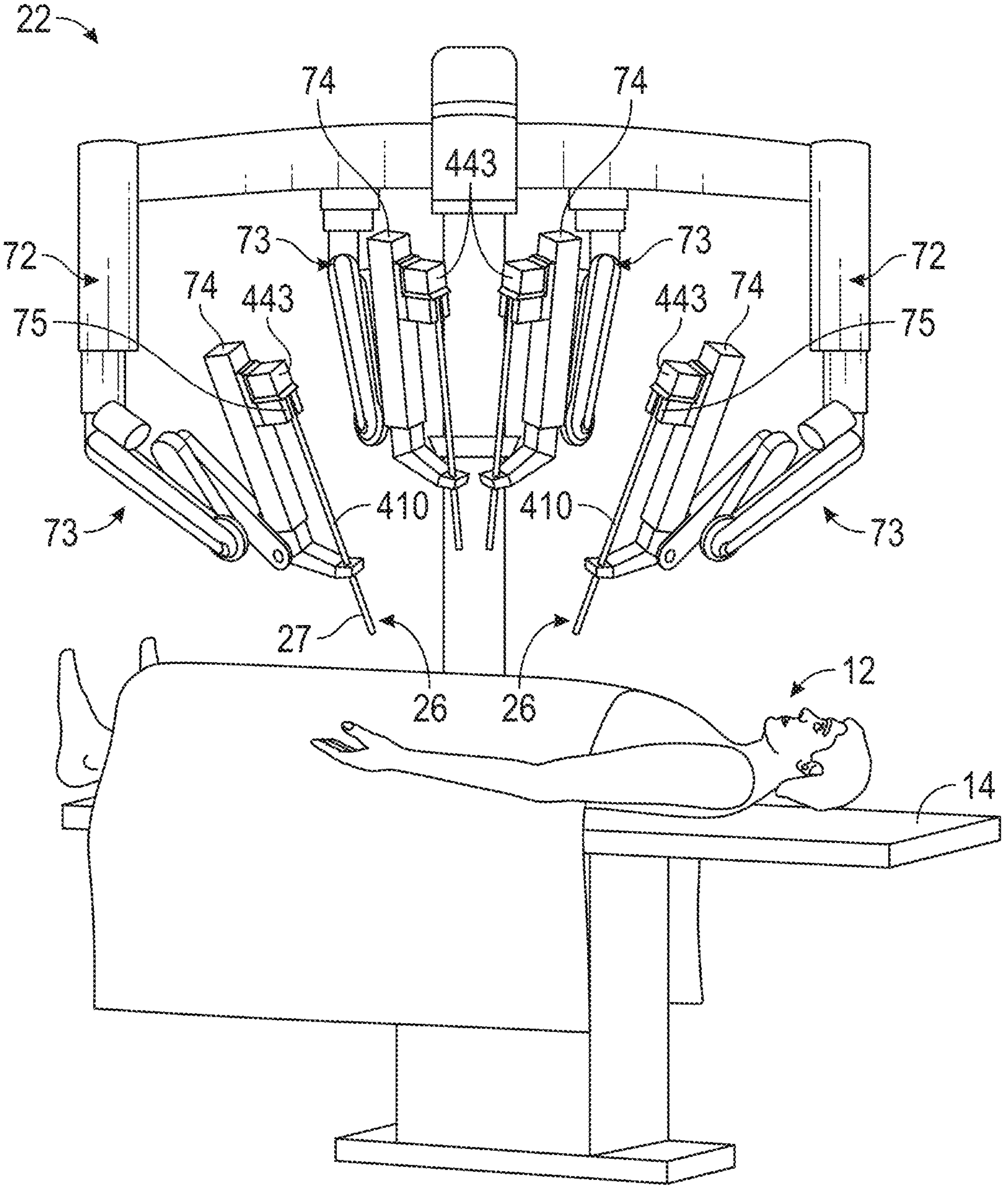
FIG. 3 is a perspective view of a manipulator unit of a minimally invasive teleoperated surgical system.

FIG. 3 is a perspective view of a manipulator unit 22 of the example minimally invasive teleoperated surgical system 10, in accordance with some embodiments. The manipulator unit 22 includes four manipulator support structures 72. Each manipulator support structure 72 includes articulated support structures 73 that are pivotally mounted end-to-end and a pivotally mounted support spar 74. A respective surgical instrument carriage 75, which includes motors to control instrument motion, is mounted at each support spar 74. Additionally, each manipulator support structure 72 can optionally include one or more setup joints (e.g., unpowered and/or lockable) at the junctions of the articulated support structures 73 and at a junction with a spar 74. A carriage 75 can be moved along a spar 74 to position the carriage 75 at different locations along the spar 74. Thus, the spars 74 can be used to position the attached surgical instrument carriage 75 in relation to a patient 12 for surgery. Each surgical instrument 26 is detachably connected to a carriage 75. While the manipulator unit 22 is shown as including four manipulator support structures 72, more or fewer manipulator support structures 72 can be used. In general, at least one of the surgical instruments will include a vision system that typically includes an endoscopic camera instrument for capturing video images and one or more video displays for displaying the captured video images that are coupled to one of the carriages 75.

In one aspect, a carriage 75 houses multiple teleoperated actuators such as motors (not shown) that impart motion to a tension member, such as a cable drive members, that include drive shafts and capstans (not shown), that in turn, drive cable motions that the surgical instrument 26 translates into a variety of movements of an end effector portion of the surgical instrument 26. In some embodiments, the teleoperated actuators in a carriage 75 impart motion to individual components of the surgical instrument 26 such as end effector wrist movement or jaw movement, for example.

A surgeon manipulates the master control input devices 36, 38 to control an instrument end effector. An input provided by a surgeon or other medical person to a control input device 36 or 38 (a "master" command) is translated into a corresponding action by the surgical instrument 26 (a corresponding "slave" response) through actuation of one or more remote motors. A flexible wire cable-based force transmission mechanism or the like is used to transfer the motions of each of the remotely located teleoperated motors to a corresponding instrument-interfacing actuator output located at an instrument carriage 75. In some embodiments, a mechanical adapter interface 76 mechanically couples an instrument 26 to actuators 442 (shown in FIGS. 4-5) within an instrument carriage to control motions inside the instrument 26. The surgical instrument 26 may be mechanically coupled to a first actuator (not shown), which may control a first motion of the surgical instrument such as longitudinal (z-axis) rotation. The surgical instrument 26 may be mechanically coupled to a second actuator (not shown), which may control second motion of the surgical instrument such as planar two-dimensional (x, y) motion. The surgical instrument 26 may be mechanically coupled to a third actuator, which may control third motion of the surgical instrument such as opening and closing of jaws of an end effector, for example.

In one aspect, the carriage 75 houses multiple teleoperated actuators such as motors (not shown) that impart motion to cable drive members, such as drive shafts and capstans (not shown), that in turn, drive cable motions that the surgical tool 26 translates into a variety of movements of an end effector on the surgical tool 26. In some embodiments, the teleoperated actuators in the carriage 75 impart motion to individual components of the surgical tool 26 such as end effector wrist movement or jaw movement, for example. A surgeon manipulates the master control inputs 36, 38 to control a tool end effector. An input provided by a surgeon or other medical person to a control input 36 or 38 (a "master" command) is translated into a corresponding action by the surgical tool 26 (a "slave" response) through actuation of one or more remote motors. A flexible wire cable-based force transmission mechanism or the like is used to transfer the motions of each of the remotely located teleoperated motors to a corresponding tool-interfacing actuator, such as a capstan drive, located at a carriage 75. In some embodiments, a mechanical adapter interface 76 mechanically couples cable drive members within a tool 26 to motors within a carriage.

The term "surgical tool" is used herein to describe a medical device for insertion into a patient's body and use in performing surgical or diagnostic procedures. A surgical tool typically includes an end effector associated with one or more surgical tasks, such as jaws, a needle driver, a shears, a bipolar cauterizer, a tissue stabilizer or retractor, a clip applier, an anastomosis device, an imaging device (e.g., an endoscope or ultrasound probe), and the like. Some surgical tools used with embodiments further provide an articulated support (sometimes referred to as a "wrist") for the end effector so that the position and orientation of the end effector can be manipulated with one or more mechanical degrees of freedom in relation to the tool's shaft 410. Further, many surgical end effectors include a functional mechanical degree of freedom, such as jaws that open or close, or a knife that translates along a path. Surgical instruments appropriate for use in one or more embodiments of the present disclosure may control their end effectors (surgical tools) with one or more rods and/or flexible cables. In some examples, rods, which may be in the form of tubes, may be combined with cables to provide a pull, push, or combined "push/pull" or "pull/pull" control of the end effector, with the cables providing flexible sections as required. A typical elongated tool shaft 410 for a surgical tool is small, for example five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The rods and cables must fit within the elongated tool shaft 410 and be able to control the end effector through the wrist joint. The cables may be manufactured from a variety of metal (e.g., tungsten or stainless steel) or polymer (e.g., high molecular weight polyethylene) materials.

Figures 4A, 4B:
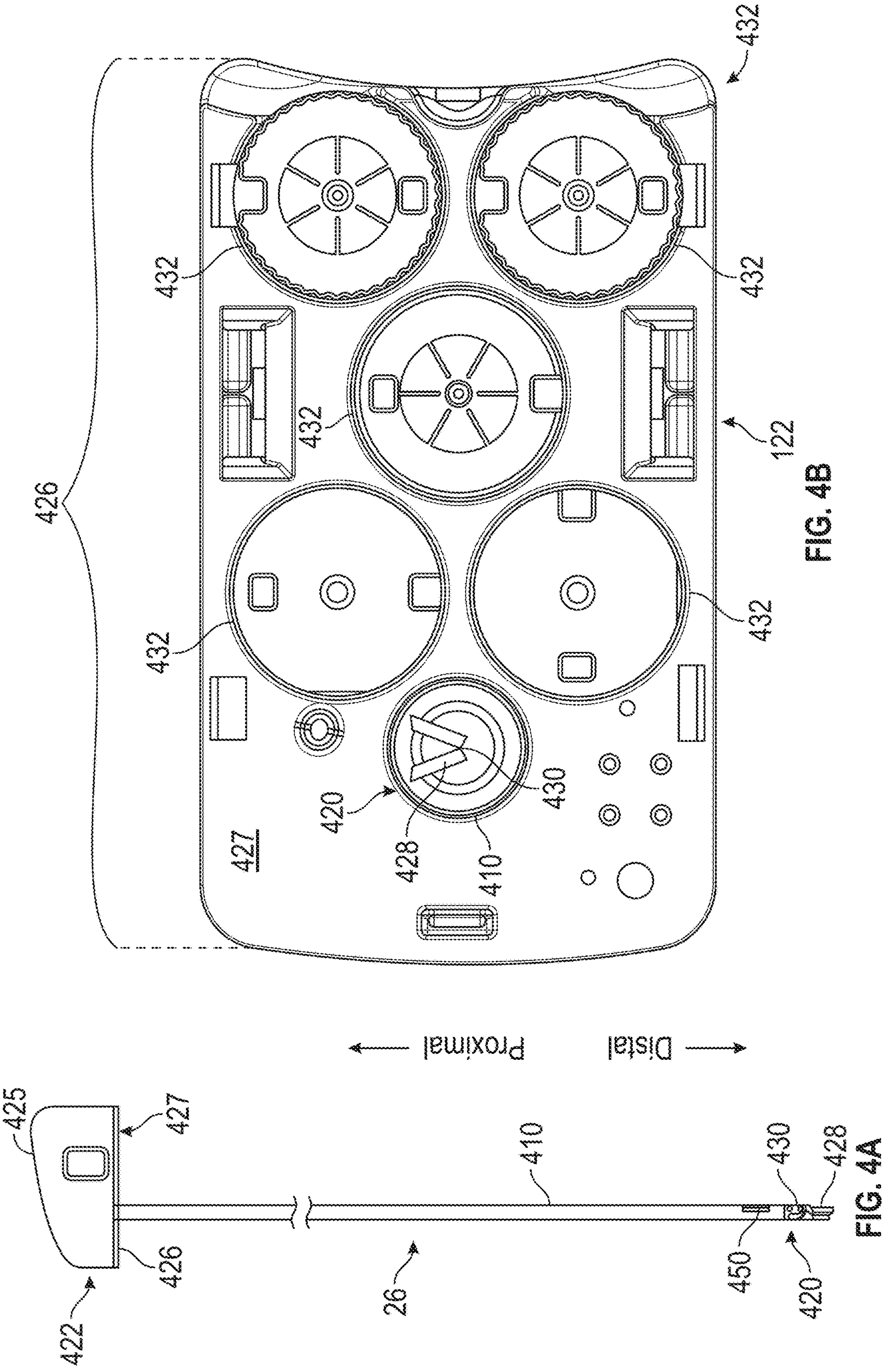
FIG. 4A is an illustrative side view of a surgical tool including a distal portion and a proximal drive assembly coupled to one another by an elongate shaft defining an internal bore.
FIG. 4B is an illustrative bottom view of the surgical tool of FIG. 4A showing the control surface of input device.

FIG. 4A is an illustrative side view of a surgical tool 26 including a tool shaft distal portion 420 and a proximal drive assembly 422 coupled to one another by an elongate shaft 410 defining an internal bore. As used herein the term "proximal" indicates a location closer to a manipulator arm, and the term "distal" indicates a location more distant from the manipulator arm. Drive assembly 422 includes a housing 425 supporting an input interface 426. Input interface 426 includes an instrument control surface 427. The input interface facilitates controlled adjustment of the instrument's end effector via a drive cable extending along an internal bore of the elongated tool shaft 410. Input interface 426 provides mechanical connections to other control features of surgical instrument 26. An elongated force sensor 450 is located within the shaft 410, coaxially aligned with a longitudinal axis of the shaft 410, at the tool shaft distal portion 420. The force sensor is anchored to the tool shaft 410 so that forces imparted to the shaft are transmitted to the force sensor 450.

During use, instrument control surface 427 of input interface 426 couples to a surgical tool carriage 75 (see FIG. 3), which s motor-driven rotational torques to drive inputs 432 at the control surface 427 to control the surgical tool 26, as generally described above. Distal portion 420 of surgical tool 26 may include any one of a variety of end effectors, such as the jaws 428 shown, a needle driver, a cautery device, a cutting tool, an imaging device (e.g., an endoscope or ultrasound probe), or a combined device that includes a combination of two or more various tools and imaging devices. Further, in the illustrated embodiment, end effector jaws 428 are coupled to the elongate tool shaft 410 by a wrist joint 430, which allows the orientation of the jaws to be manipulated with reference to the elongated tool shaft 424.

FIG. 4B is an illustrative bottom view of the surgical tool 26 of FIG. 4A showing the control surface 427 of input interface 426. It will be understood that the control surface 427 is positioned over a carriage 75, which includes actuators such as motors (not shown) controlled by control signals produced in response to user input at the control inputs 36, 38, for example. As shown, drive interface 426 includes multiple drive member inputs 432, each of which governs a different aspect of movement by wrist joint 430 and end effector jaws 428. Of course, more or fewer drive inputs 432 can be provided in different implementations. When control surface 427 is coupled to tool carriage 75, each of drive inputs 432 interfaces with an actuator (not shown) within the carriage 75 that drives the drive input. In this example, drive inputs 432 are configured to form a direct mechanical engagement with respective rotary actuators (e.g., servo motors) of tool carriage 75. Other suitable configurations for rotary or linear mechanical power transmission can also be used (e.g., indirect mechanical couplings, including speed and/or torque converters, fluid couplings, and/or electrical couplings). As explained more fully below, each of drive inputs 432 is part of a limited slip capstan and drive shaft assembly that operates a drive cable controlling movement of an end effector such as jaws 428, for example.

Force Sensing, Haptic Feedback, and Cable Slippage

Figure 5A:
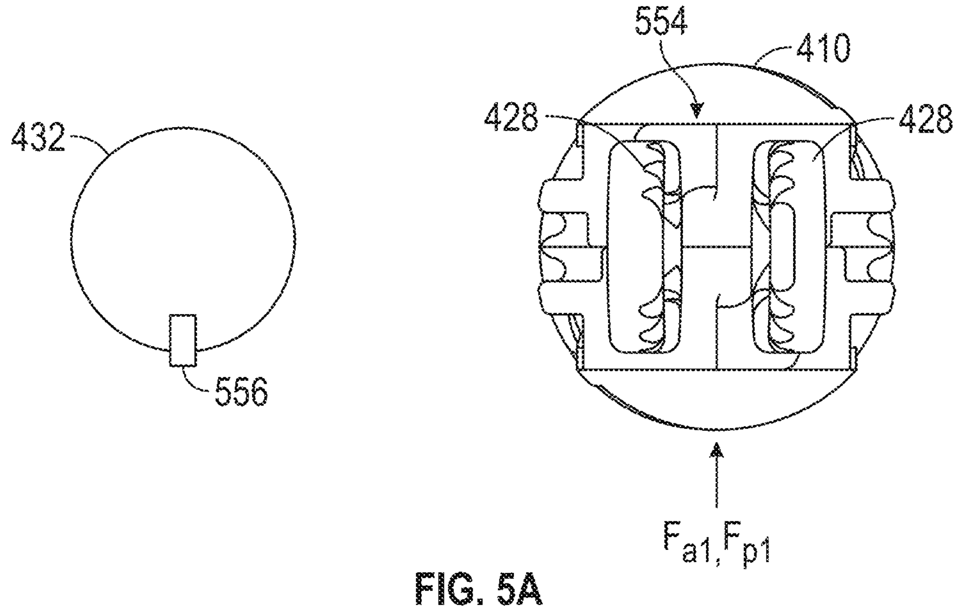
FIG. 5A is an illustrative drawing representing a relationship between an example first rotational orientation of a cable drive member and an example first roll position of an end effector that are properly aligned with reference to one another.
Figure 5B:
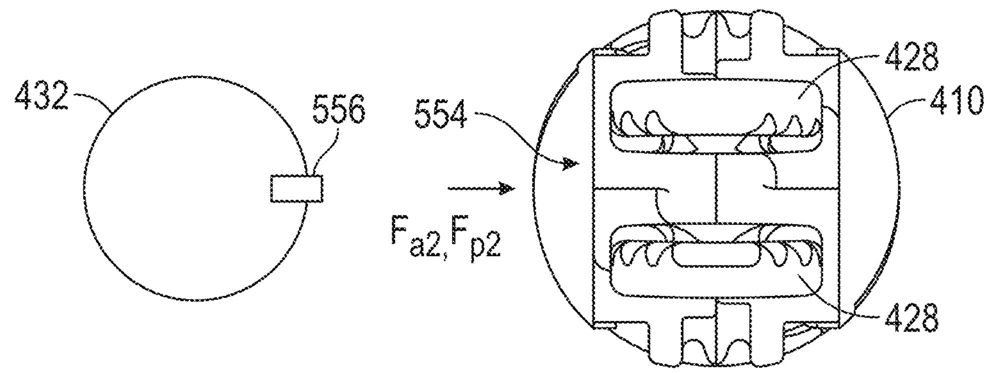
FIG. 5B is an illustrative drawing representing a relationship between an example second rotational orientation of the cable drive member and an example second roll position of the end effector that are properly aligned with reference to one another.
Figure 6:
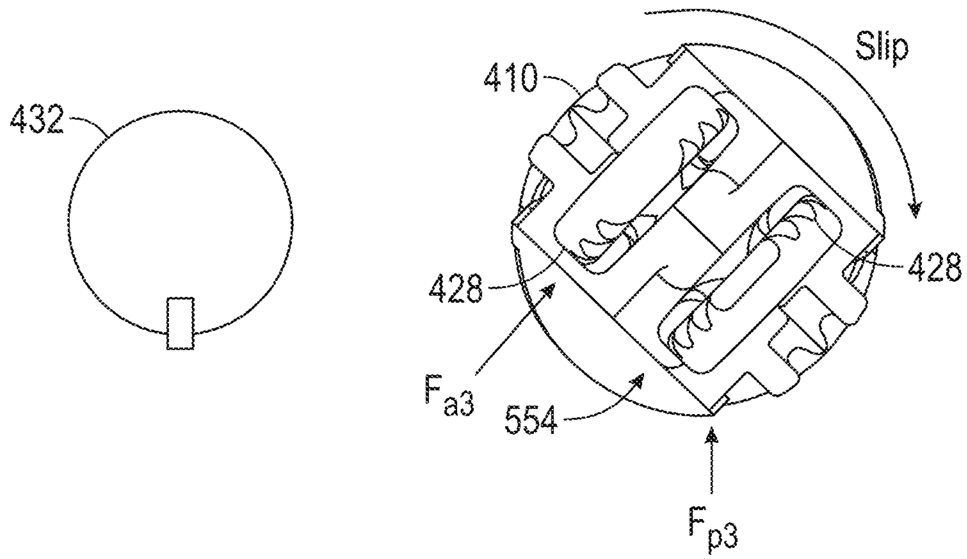
FIG. 6 is an illustrative drawing representing a relationship between the example first rotational orientation of the cable drive member and an example third roll position of the end effector that are misaligned with reference to one another.

FIG. 5A is an illustrative drawing representing a relationship between an example first rotational orientation of a cable drive element 432 and an example first roll position of an end effector 554 that are properly aligned with reference to one another. FIG. 5B is an illustrative drawing representing a relationship between an example second rotational orientation of the cable drive element 432 and an example second roll position of the end effector 554 that are properly aligned with reference to one another. FIG. 6 is an illustrative drawing representing a relationship between the example first rotational orientation of the cable drive element 432 and an example third roll position of the end effector 554 that are misaligned with reference to one another. In FIGS. 5A-6, a hashmark 556 is used for illustrative purposes to indicate the rotational orientation of the of the cable drive element 432. FIGS. 5A-6 show illustrative end views of an end effector 554 having opposed jaws 428 extending from a distal end portion of a tool shaft 410.

As used herein, proper alignment refers to a prescribed relationship between rotational orientation of a cable drive element 432 and roll position of an end effector 554 with reference to one another. Referring to FIGS. 5A-5B, in which the cable drive element 432 and the end effector 554 are properly aligned, an example prescribed relationship is represented by the hashmark 556 facing in a direction parallel to the faces of the opposed jaws 428. In FIG. 5A, the hashmark 556 faces vertically downward and the opposed jaws 428 are vertically oriented. In FIG. 5B, the hashmark 556 faces horizontally to the right and the opposed jaws 428 are horizontally oriented.

As used herein, misalignment refers to relationship between rotational orientation of a cable drive element 432 and roll position of an end effector 554 with reference to one another that does not match a prescribed relationship. Referring to FIG. 6, the hashmark 556 does not face in a direction parallel to the faces of the opposed jaws 428. Therefore, in FIG. 6, the cable drive element 432 and the end effector 554 are misaligned.

The cable drive element 432 and the end effector 554 can be put into a prescribed alignment during a calibration process that can occur during an assembly or manufacturing, for example. Relationships are determined between amount of cable played out between the cable drive element 432 and the end effector during a range of cable drive element rotational orientations and corresponding end effector roll positions, for example. Then, a portion of the cable is secured at the cable drive element 432 and a portion of the cable is secured at the end effector 554 to maintain the determined relationships, for example. Misalignment can arise due to cable slippage at the cable drive member 432, for example, that results in disrupting the prescribed relationship by changing the amount of cable that is played out between the cable drive element 432 and the end effector 554.

FIG. 5A shows that in the first rotational orientation, the cable drive element 432 is rotated such that the hashmark 556 is downward facing, and that in the first roll position, the opposed jaws 428 are aligned vertically. As shown, a first applied force Fa1 is imparted to the end effector 554 in a first direction. Computer processors located in the auxiliary unit 24 use the rotational orientation of the cable drive element 432 to determine haptic feedback to present a first perceived force Fp1 at control inputs 36, 38. As shown, since the cable drive element 432 and the end effector 554 are properly aligned with reference to one another, a direction of the first perceived force Fp1 determined by the processors, matches a direction of the first applied force Fa1. Accordingly, based upon the first perceived force Fp1, a user can accurately determine commands to provide at control inputs 36, 38 to control the end effector 554 in response to the first applied force Fa1.

FIG. 5B shows that in the second rotational orientation, the cable drive element 432 is rotated such that the hashmark 556 is rightward facing, and that in the second roll position, the opposed jaws 428 are aligned horizontally. As shown, a second applied force Fa2 is imparted to the end effector 554 in a second direction. Computer processors located in the auxiliary unit 24 use the rotational orientation of the cable drive element 432 to determine haptic feedback to present a second perceived force Fp2 at control inputs 36, 38. As shown, since the cable drive element 432 and the end effector 554 are properly aligned with reference to one another, a direction of the second perceived force Fp2 determined by the processors, matches a direction of the second applied force Fa2. Accordingly, based upon the second perceived force Fp2, a user can accurately determine commands to provide at control inputs 36, 38 to control the end effector 554 in response to the second applied force Fa2.

FIG. 6 shows the cable drive element 432 in the first rotational orientation with the hashmark 556 downward facing and shows the opposed jaws 428 aligned diagonally in the third roll position. As shown, a third applied force Fa3 is imparted to the end effector 554 in a third direction. Computer processors located in the auxiliary unit 24 use the rotational orientation of the cable drive element 432 to determine haptic feedback to present a third perceived force Fp3 at control inputs 36, 38. As shown, since the cable drive element 432 and the end effector 554 are improperly aligned with reference to one another, a direction of the third perceived force Fp3 determined by the processors, does not match a direction of the third applied force Fa3. Accordingly, a user is not able to accurately determine commands to provide at control inputs 36, 38 to control the end effector 554 in response to the second applied force Fa2 based upon the second perceived force Fp2.

It will be appreciated that small misalignments between the cable drive element 432 and the end effector 554 can result in small misalignments of an applied force and a perceived force. Such small misalignments may not result in a significant impact upon the accuracy of a user commands provided at the control input devices 36, 38 in response to the applied force. However, a misalignment of ninety-degrees, for example, can result in a perceived force direction that is opposite to an applied force direction, which can result in a user imparting commands at the control input devices 36, 38, that cause motion of the end effector 554 that is in a direction opposite to a direction of motion intended by the user.

Limited Slip Capstan and Drive Shaft Assembly

Figure 7A:
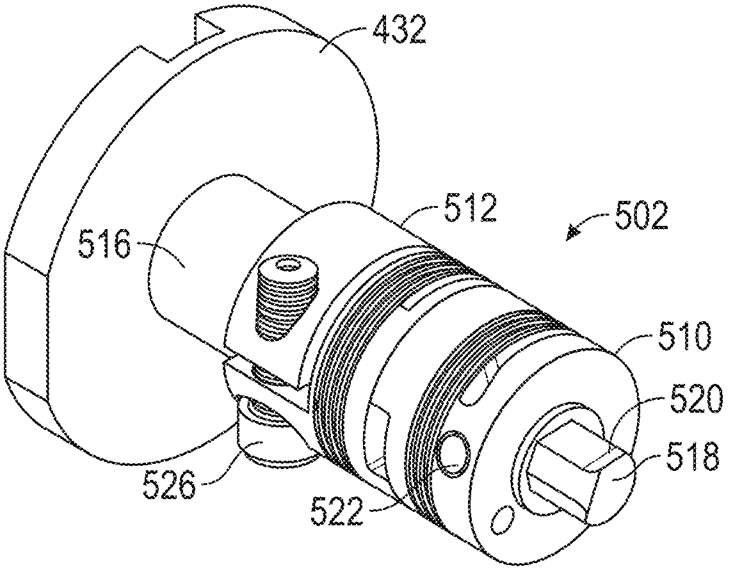
FIG. 7A is an illustrative perspective view of a limited slip capstan and drive shaft assembly in accordance with some embodiments.
Figure 7B:
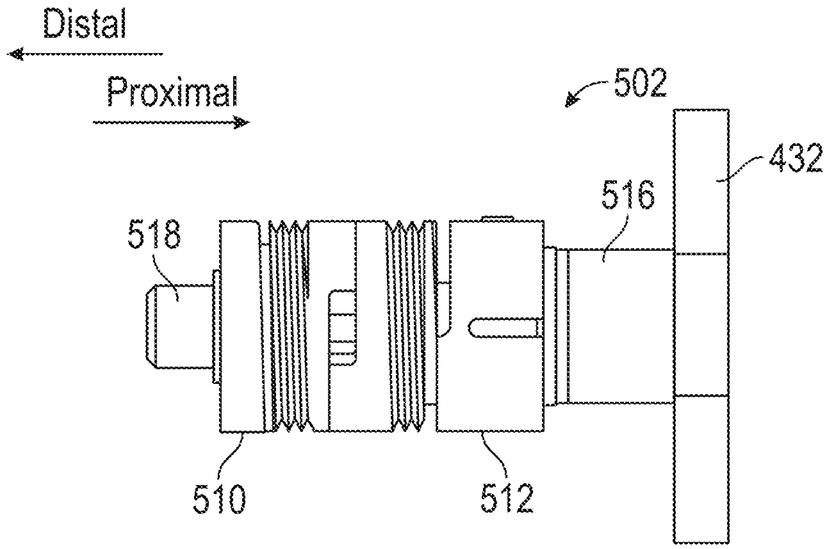
FIGS. 7B-7C are opposite side views of the limited slip capstan and drive shaft assembly.
Figure 7C:
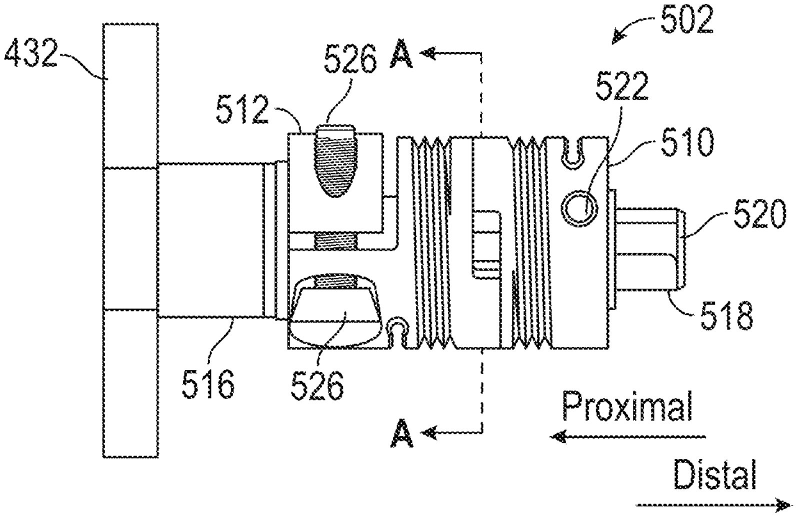
Figure 7D:
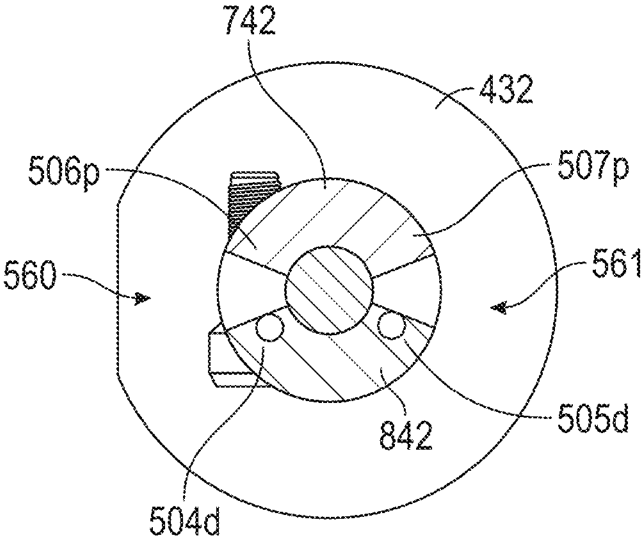
FIG. 7D is a cross-sectional view along lines A-A in FIG. 7C showing the opposed slip stop shoulders.
Figure 7E:
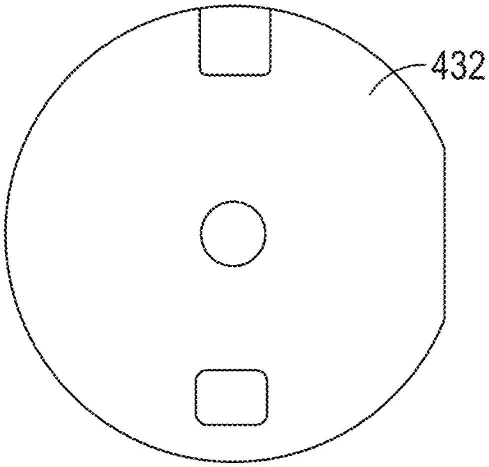
FIG. 7E is an illustrative drawing showing an end view showing a steering input drive disc.

FIG. 7A is an illustrative perspective view of a limited slip capstan and drive shaft assembly 502 in accordance with some embodiments. FIGS. 7B-7C are opposite side views of the limited slip capstan and drive shaft assembly 502 of the embodiment of FIG. 7A. FIG. 7D is a cross-sectional view along lines A-A in FIG. 7C showing a first second-direction extending slip stop shoulder **504*d*, a second second-direction extending slip stop shoulder 505*d*, a first first-direction extending slip stop shoulder 506*p*, and a second first-direction extending slip stop shoulder 507*p*, of the embodiment of FIG. 7A. In the example shown, the first direction is a distal direction and the second direction is a proximal direction. It is noted that for the example back end configuration shown herein, the drive shaft 514 extends parallel to a longitudinal axis of the instrument shaft 410, and therefore the drive shaft has distal and proximal portions oriented similarly with the tool shaft. In an alternative example (not shown), the capstan axis of rotation is perpendicular to the instrument shaft axis, in which case the drive shaft has proximal and distal portions that are still oriented relative to the surgical site and manipulator. FIG. 7E is an illustrative drawing showing an end view showing a drive input 432**

(e.g., a drive input disk) of the embodiment of FIG. 7A. The limited slip capstan and drive shaft assembly 502 includes a first capstan 510, a second capstan 512, and drive shaft (described below), which are components of the input interface 426.

Figure 8:
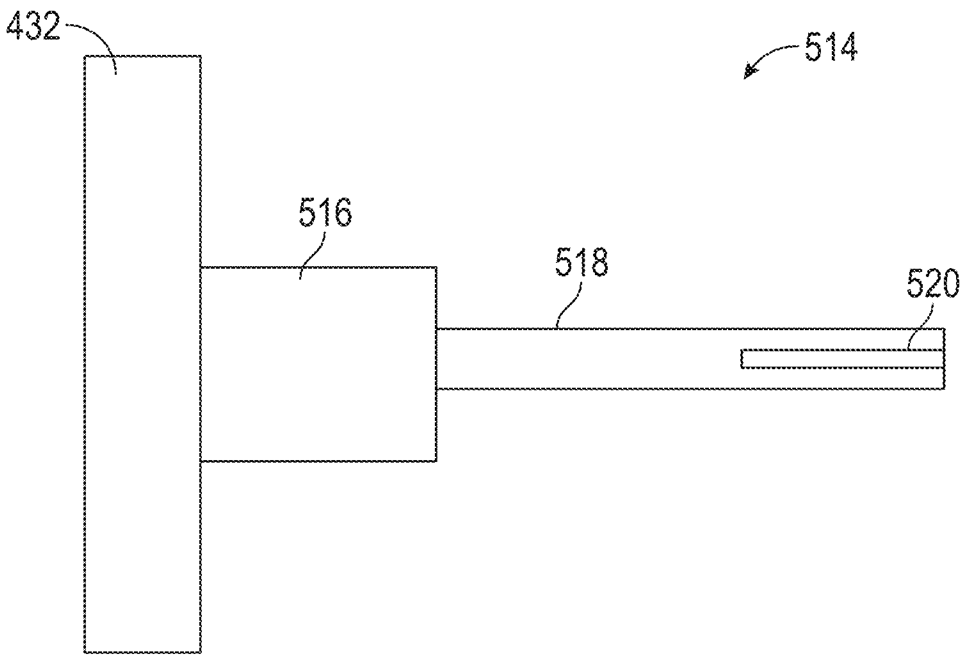
FIG. 8 is an illustrative view of a drive shaft in accordance with some embodiments.

FIG. 8 is an illustrative view of the drive shaft 514 in accordance with some embodiments. The drive shaft 514 includes the disc-shaped drive input 432 at a proximal end portion thereof, a cylindrical support base portion 516 extends distally outward from the input drive disc 432, and an elongate cylindrical rod portion 518 extends distally outward from the support base portion 516. The support base portion 516 has a larger diameter than the cylindrical rod portion 518. In some embodiments, the drive input 432, support base 516, and the rod 518 are formed of thermoplastic (e.g., nylon or polycarbonate) that are overmolded around a metal support stem. The first and second capstans 510, 512 are tubular and annular. Through-bores are defined in the first and second capstans 510, 512 and are sized to permit passage of the rod portion 518 therethrough.

Referring to FIGS. 7A-7C, the first capstan 510 is mounted upon the rod portion of the drive shaft between the second capstan 512 and a first end portion of the drive shaft. The second capstan is mounted upon the rod portion of the drive shaft between the support base 516 and the first capstan. A first portion of the rod includes a notch feature 520 for engagement with a locking pin 522 that may be inserted within the first capstan to interference lock the first capstan 510 to the rod 518 to prevent, or at least limit, relative rotation between them. In the example shown herein, the first end portion of the drive shaft is a proximal end portion. In some examples the distal first capstan 510 includes a radial threaded hole 524 (see FIG. 9A) sized to interfit with a threaded pin 522 that engages with the notch portion 520 of the rod to secure through friction locking the first capstan 510 to the rod 518.

As discussed in detail below, when first and second capstans 510, 512 are fully engaged with drive shaft 514, relative rotation between drive shaft 514 and the first and second capstans 510, 512 is at least inhibited (or entirely prevented, in some examples). In the fully engaged state, friction between the end of the pin 522 and the notch 520 can be overcome if the torque on the capstan is large enough allowing for relative rotation of the first capstan and the drive shaft 514. In a fully disengaged state, the capstans may be carried on the rod portion 518 of the drive shaft 514, but relative rotation between the capstans 510, 512 and the rod 518 is freely permitted (i.e. uninhibited). During a pre-tensioning procedure, the first capstan 510 is frictionally engaged to lock the first capstan to the rod 518 to prevent relative rotation between the first capstan 510 and the rod 518 while the distal second capstan 512 is freely rotatable about the shaft.

Figure 9A:
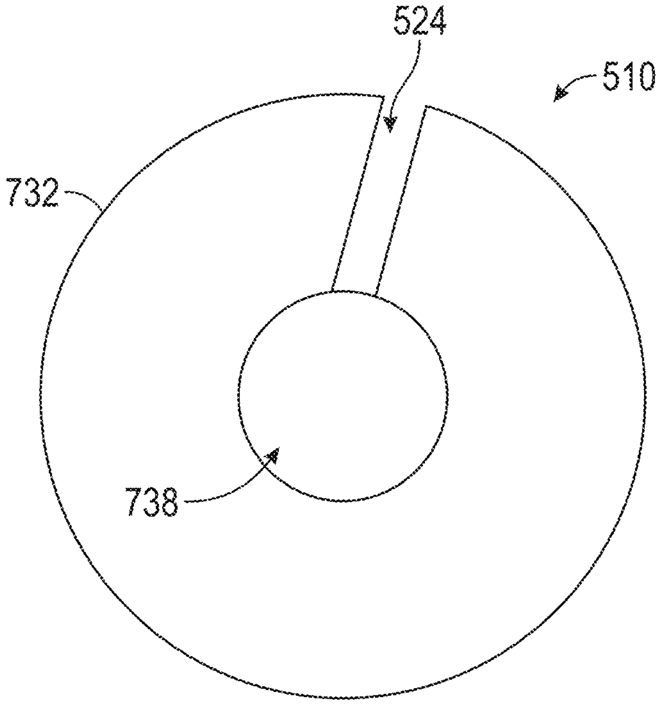
FIGS. 9A-9C are illustrative drawings showing a cross-sectional end view (FIG. 9A) along lines B-B in FIG. 9B, a side view (FIG. 9B), and an end view (FIG. 9C) of the first capstan.
Figure 9B:
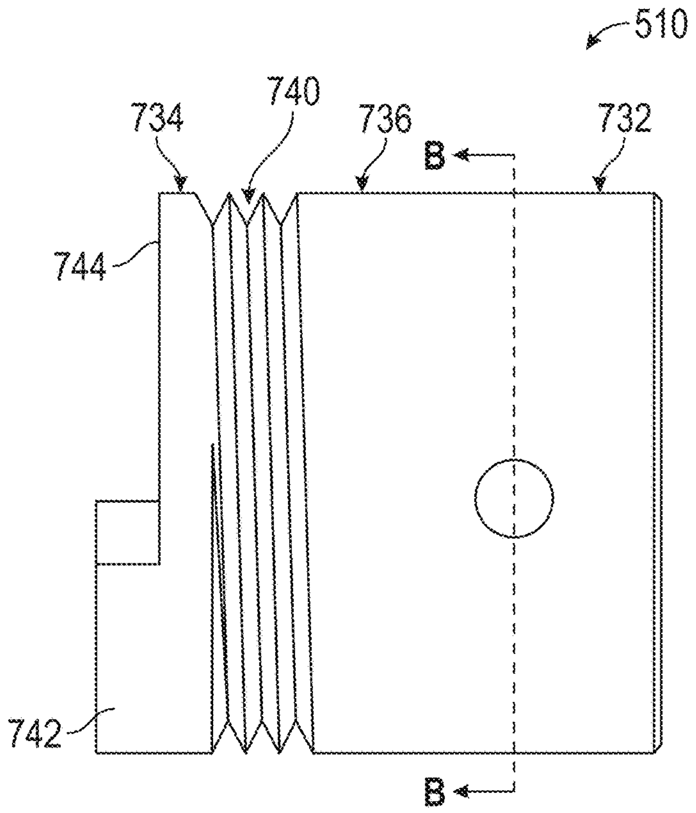
Figure 9C:
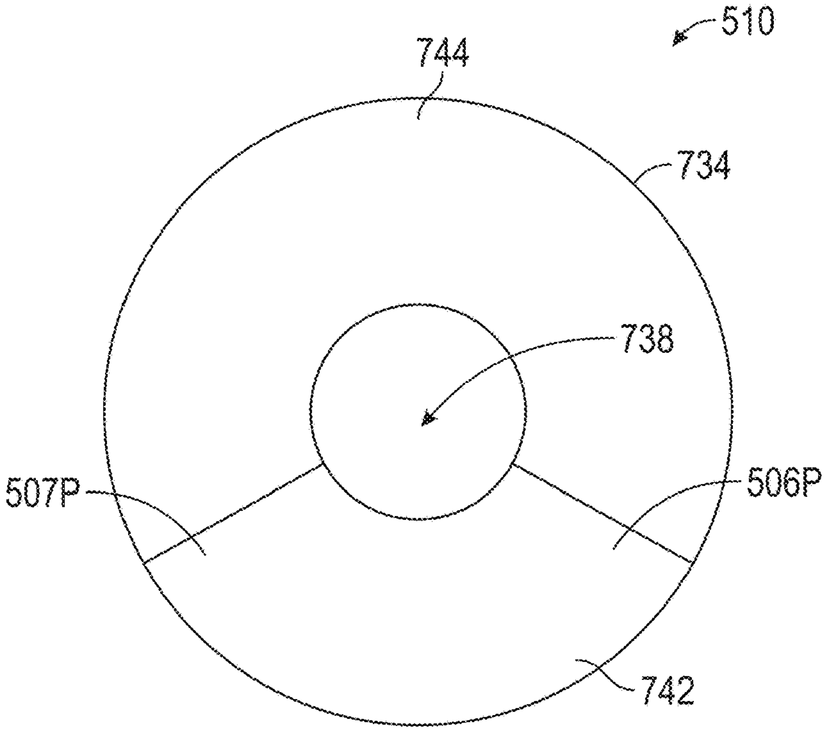

FIGS. 9A-9C are illustrative drawings showing a cross-sectional end view (FIG. 9A) along lines B-B in FIG. 9B, a side view (FIG. 9B), and an end view (FIG. 9C) of the first capstan 510. The first capstan is a monolithic, substantially cylindrical structure including a first end portion 732, a second end portion 734, and a center portion 736. The first capstan 510 includes a central through-bore 738 traversing its first end, center, and second end portions. The center portion 736 includes an outwardly facing helical groove 740 to guide the winding of a cable end 1020 (see FIG. 12). The pin slot 524 is formed in the first end portion 732 of the first capstan to receive the pin 522 to secure the first capstan 510 to the rod 518.

Referring to FIG. 9C, the second end portion 734 of the first capstan 510 includes a first first-direction extending slip-stop shoulder 506*p* and a second first-direction extending slip-stop shoulder 507*p*. Slip-stop shoulder 506*p*,507*p* extend in a first direction, toward the second capstan 512, at a proximal end face of the proximal second end portion 734. The first-direction extending first and second proximal slip-stop shoulders 506*p*, 507*p* are angularly separated from one another in a range between 135° and 170°, and preferably about 140 degrees. As explained below, second-direction extending first and second shoulders 504*d*, 505*d* also are angularly separated in a range between 135° and 170°, and preferably about 140 degrees. As explained below, the shoulders are aligned during pre-tensioning to be equally spaced apart. For shoulders are angularly spaced by 135 degrees, equal angular offset spacing is 45 degrees, and even if a pair of opposed shoulder abut, the angular offset spacing between non-abutting shoulders is 90 degrees, which is an outer safety limit at which perceived force Fp is opposite applied force Fa as explained above. For shoulders are angularly spaced by 170 degrees, equal angular offset spacing is 10 degrees, and even if a pair of opposed shoulder abut, the angular offset spacing between non-abutting shoulders is 40 degrees, which is within the outer safety limit. For shoulders are angularly spaced by 140 degrees, equal angular offset spacing is 40 degrees, and even if a pair of opposed shoulder abut, the angular offset spacing between non-abutting shoulders is 80 degrees, which is within the outer safety limit.

In some embodiments, the first capstan 510 is generally circular in cross-section, and the second end portion 734 includes an arcuate first-direction tooth portion 742 that extends in the first direction and that defines the first and second first-direction extending slip-stop shoulders 506*p*, 507*p* at opposite ends thereof, separated from one another by the above angular range. Referring to FIGS. 9B-9C, the arcuate first-direction extending tooth portion extends opposite an inset end face portion 744 of the second end portion 734 first capstan 510.

Figure 10A:
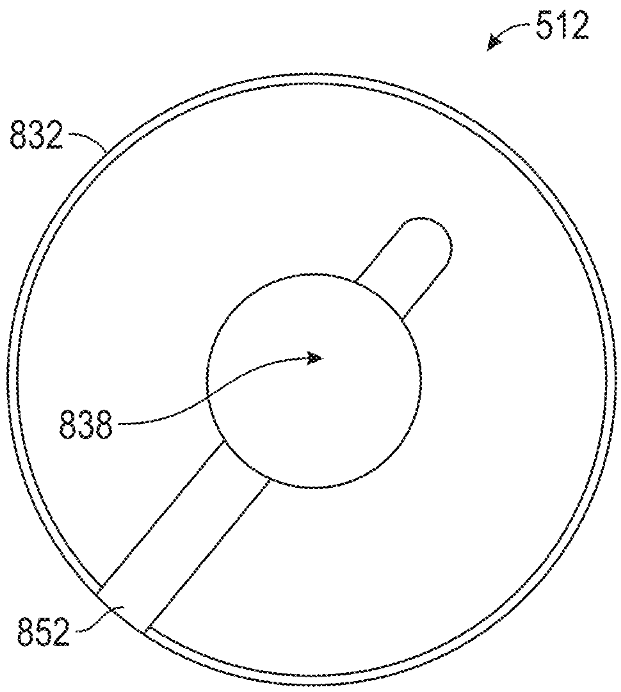
FIGS. 10A-10C are illustrative drawings showing a proximal (bottom) end view (FIG. 10A), a side view (FIG. 10B), and a cross-sectional view (FIG. 10C) along lines B-B in FIG. 10A of the distal second capstan.
Figure 10B:
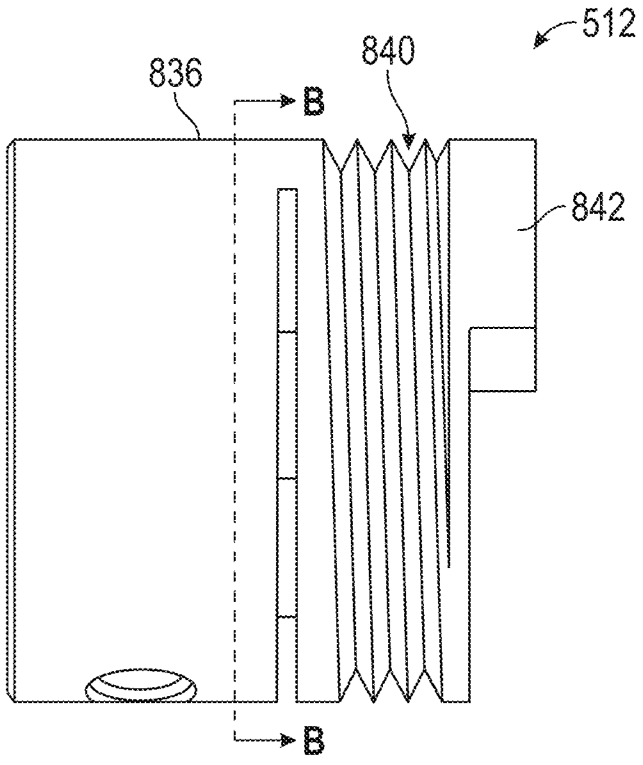
Figure 10C:
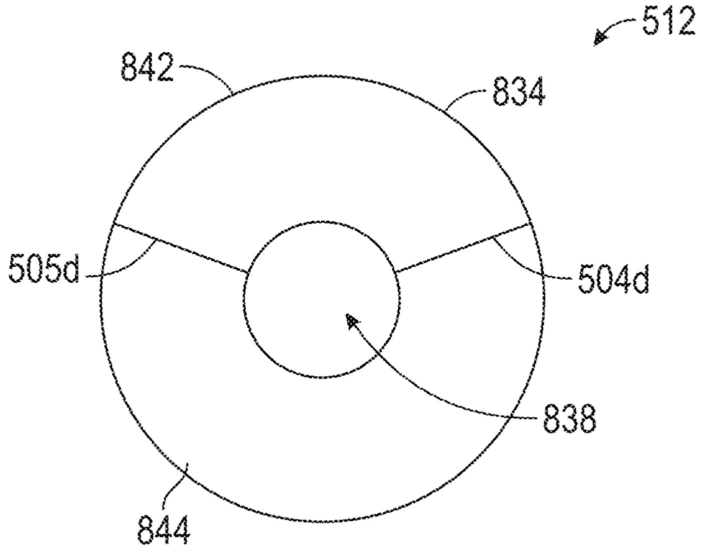

FIGS. 10A-10C are illustrative drawings showing a proximal (bottom) end view (FIG. 10A), a side view (FIG. 10B), and a cross-sectional view (FIG. 10C) along lines B-B in FIG. 10A of the distal second capstan 512. The second capstan 512 is a monolithic substantially cylindrical structure including a first end portion 832, a distal second end portion 834 and a center portion 836. The second capstan 512 defines a central through-bore 838 traversing its distal, center and proximal portions. The center portion 836 includes an outwardly facing helical groove 840 to guide the winding of a cable end 1022 (see FIG. 12). The first end portion 832 of the second capstan 512 is configured as a split clamp that defines a vertical slot 852 that extends parallel to a center axis and traverses a portion of the second capstan 512, and a horizontal cross-pin hole 910 (see FIG. 11) intersects the slot to receive a cross-pin to provide a clamping force to squeeze the first end portion 832, at the vertical slot 852, to clamp the first end portion 832 to the rod. The clamping force produces a friction engagement between the rod 518 and a surface of the inner bore 838 of the first end portion 832 of the clamp 512 to prevent relative rotation between them. In some embodiments the second capstan 512 includes a threaded horizontal pin hole (not shown) sized to engage with a threaded cross-pin 526 (see FIGS. 7A, 7C) that acts as a fastener to squeeze closed the vertical slot 852 to fasten the second capstan 512 to the rod 518 using a frictional clamping force.

Referring to FIG. 10C, the distal second end portion 834 of the second capstan 512 includes first and second distal slip-stop shoulders 504*d*, 505*d* that extend in a distal direction, toward the first capstan, at a distal end face of the distal second end portion. The second-direction extending first and second distal slip-stop shoulders 504*d*, 505*d* are angularly separated from one another, at a distal end face of the distal second end portion, in a range between 135° and 170°. In some embodiments, the second capstan 512 is generally circular in cross-section, and the distal second end portion 832 includes an arcuate distal tooth portion 842 that extends in the distal direction and that defines the first and second distal slip-stop shoulders at opposite ends thereof, separated from one another by the above angular range. Referring to FIGS. 10B-10C, the arcuate distal tooth portion 842 upstands opposite an inset end face portion 844 of the distal second end portion 834 second capstan 512.

Referring to FIGS. 7A-7C, the drive shaft 514 and the first and second capstans 510, 512 are simultaneously coaxially aligned to one another by inserting the rod portion 518 of drive shaft 514 through the center bores 738, 838 of the first and second capstans 510, 512. In some embodiments, during a pre-tensioning process, the control cables wound around the first and second capstans are pre-tensioned so that there is always tension on the control cables that extend from the capstan to the distal end effector. This pre-tensioning eliminates cable slack and ensures little or no hysteresis between capstan rotation angle and cable translation distance for precise end effector control.

In some embodiments, cable stiffness is relatively high—in excess of 250 lbf/in and preferably, approximately 500 lbf/in. Thus, for example moving two-thousandths of an inch gives two pounds pre-load. In some embodiments, desired pre-load tensioning is in a range two to five pounds. So, for example, movement of about four-thousandths of an inch of arc travel may be required to go from un-tensioned to tensioned. Proximal and distal teeth 742, 842 may be aligned with one another prior to pre-tensioning so that arcuate spacing between adjacent second-direction extending and first-direction extending first slip-stop shoulders 504*d*, 506*p* matches arcuate spacing between adjacent second-direction extending and first-direction extending second slip-stop shoulders 505*d*, 507*p*. Since pre-tensioning arc travel typically generally will not result in significant changes in the angular spacing between the capstans, their angular spacing will not change significantly during pre-tensioning. Thus, provided that adjacent shoulders are sufficiently spaced apart prior to pre-tensioning, they will be adequately spaced apart after pre-tensioning.

During the pre-tensioning process, the first capstan 510 is engaged to the shaft 514 for simultaneous rotation with the drive shaft 514 while the second capstan 512 is mounted to the drive shaft 514, disengaged from the shaft 514, to permit rotation of the second capstan 512 relative to the drive shaft 514. More particularly, the pin 522 is tightened to lock the first capstan to the rod 518 while the cross-pin 526 is loosened to not clamp the second capstan 512 to the rod 518. Thus, the rod 518 functions as a spindle that provides a central axis of rotation for the second capstan 512 during pre-tensioning. The first capstan 510 is locked in place on the rod so as to not rotate relative to the rod 518. Thus, during pre-tensioning, the second capstan 512 and a cable end portion 1022 (see FIG. 10) wound within its outwardly facing helical grooves 840 may be rotated relative to the rod, while the first capstan 510 and a cable end portion 1020 (see FIG. 10) wound within its outwardly facing helical grooves 740 are maintained in fixed positions relative to the rod 518. Since the cables wound around the first and second capstans are antagonistic to one another across the end effector, the cable portions 1020, 1022 thereby may be pretensioned.

Also, during cable pre-tensioning the angular offsets may be preset between the adjacent second-direction extending first shoulder 504*d* and first direction-extending first shoulder 506*p*, and between the adjacent second-direction extending second shoulder 505*d* and first-direction extending second shoulder 507*p*. Since the first capstan 510 is engaged to the shaft 514 and the second capstan 512 is disengaged from the shaft 514, the second capstan is rotated to achieve the desired angular offsets.

Referring to FIG. 7D, the first and second capstans 510, 512 are rotationally oriented relative to one another such that there are matching angular offsets between the second-direction extending first and first-direction extending first shoulders 504*p*, 505*p* and between the second-direction extending second and first-direction extending second shoulders 506*d*, 507*d*. In some examples, angular offset spacing 560 between the second-direction extending first and first-direction extending first shoulders 504*d*, 506*p* is preset to be at least forty degrees, and the angular offset spacing 561 between the second-direction extending second and first-direction extending second shoulders 505*d*, 507*p* also is preset to be at least forty degrees. As a result, in the event of capstan slippage relative to the drive shaft during normal operation the adjacent shoulders will abut one another before relative rotation of the first and second capstan reaches ninety degrees.

Figure 11:
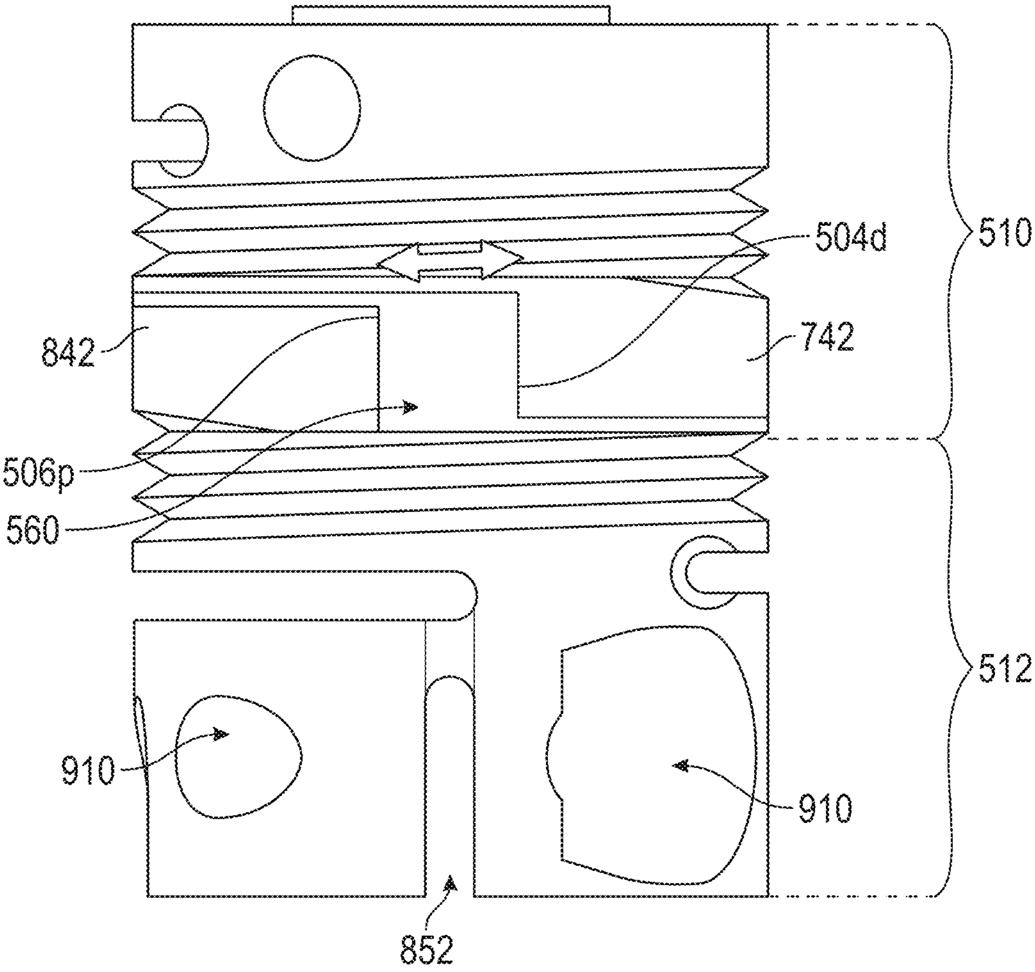
FIG. 11 is an illustrative side view showing alignment of the first and second capstans.

FIG. 11 is an illustrative side view showing the first first-direction extending first slip-stop shoulder 504*d* of the first capstan 510 opposite the first direction extending shoulder 506*p* of the second capstan 512 and showing a circumferential offset gap 560 therebetween. (The drive shaft is omitted to simplify the drawing.) The first capstan 510 has two shoulders 506*p*, 507*p* that each extend in the proximal direction. Similarly, the second capstan 512 has two shoulders 504*d*, 505*d* that extend in the distal direction. The capstans 510, 512 are coaxially aligned so that a first shoulder 506*p* of the first capstan 510 contacts a first shoulder 504*d* of the second capstan 512 at a rotational ROM limit of the capstans with reference to each other. And likewise, a second shoulder 507*p* of the first capstan 510 contacts a second shoulder 505*d* of the second capstan 512 at an opposite rotational ROM limit of the capstans 510, 512 with reference to each other. The relative rotational ROM limits are ±40 degrees in one instance, and other optional ROM limits may be used.

The second-direction extending first shoulder 504*d* is an arc end of the tooth 742, which extends from the first capstan 510. The first-direction extending first shoulder 506*p* is an opposing arc end of the distal tooth 842, which extends from the second capstan 512. During a pre-tensioning procedure, the second capstan 512 is rotatable about a center axis of the rod 518 (not shown) while the first capstan 510 is rotationally fixed relative to the center axis of the rod. The circumferential offset gap 560 due to offset between opposed second-direction extending first slip-stop shoulder 504*d* and first-direction extending first slip-stop shoulder 506*p* may be adjusted through rotation of the capstans 510, 512 relative to one another during pre-tensioning.

In some embodiments, adjacent shoulders are spaced apart by an angular distance small enough so that the adjacent shoulders will abut due to slippage of one or both capstans relative to the rod during operational use. But, the amount of the slippage will be limited so as to prevent further relative rotation of the first and second capstans 510, 512 before the relative rotational positions of the first and second capstans 510, 512 changes by ninety degrees.

Drive cables have break strengths in excess of 55 lbf, and so for strength the proximal tooth 742 and the first and second distal shoulders 504*d*, 505*d* are formed integral with a perimeter surface of the first capstan 510, and the distal tooth 842 and the first and second first-direction extending shoulders 506*p*, 507*p* are formed integral with a perimeter surface of the second capstan 512. It will be appreciated that smaller, finer teeth may be insufficiently sturdy to withstand cable loads of 55 lbf and cable stiffness in excess of 250 lbf/in and preferably, approximately 500 lbs/inch without breaking, which creates a need for larger, more robust teeth disclosed herein.

Figure 12:
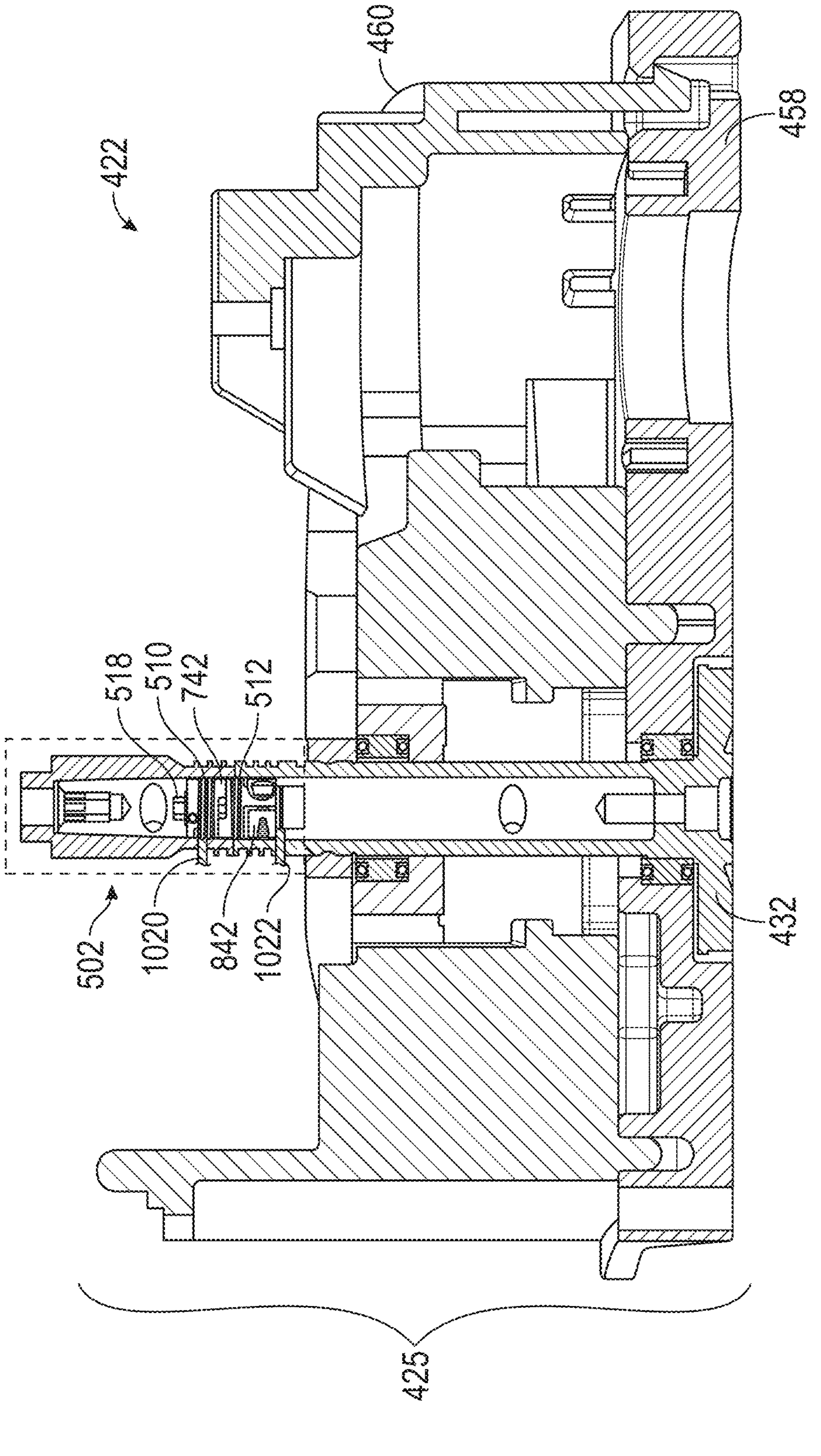
FIG. 12 is an illustrative cross-sectional view that depicts a portion of a drive assembly that includes a limited slip capstan and drive shaft assembly in accordance with some embodiments.

FIG. 12 is an illustrative cross-sectional view that depicts a portion of a drive assembly that includes a limited slip capstan and drive shaft assembly in accordance with some embodiments. In this example, carriage 425 is a multi-component structure including a base 458 mounted to a carriage 460. A drive shaft is rotatably mounted to carriage 425, with drive input 432 supported within base 458 and cylindrical rod 518 supported in carriage 460. In addition to the structural features that accommodate the rod of drive shaft, carriage 460 also includes features for mounting other operative components of the drive assembly (e.g., spools, pulleys, etc.).

As noted above, drive input 432 is configured to carry a drive cable at a limited slip capstan and drive shaft assembly. During one exemplary use, a first drive cable end portion 1020 is attached to the first capstan 510, and a second drive cable end portion 1022 is attached to the second capstan 512. In some uses, the two drive cable end portions may be opposite ends of the same cable. In other uses, the two drive cable end portions may be end portions of two different cables. In some implementations, the drive cable end portion is crimped and coupled to at least one of the first capstan and the second capstan. In some implementations, purely frictional couplings may be used to attach the ends of the drive cable to the first capstan and to the second capstan. For example, the cable ends may be wound within the helical grooves of the first and second capstans for multiple revolutions to provide sufficient surface friction to maintain the couplings intact. A middle portion of the one or more drive cables between the end portions carried by the first and second capstans of the input device 426 extends into the internal bore of the surgical tool shaft 410. As described above, the drive cable traverses the internal bore and couples to an end effector or other distal end component of the surgical tool. Mechanical power provided by an actuator of the instrument carriage is transmitted to the drive shaft via drive input 432, causing the drive shaft to rotate. With the drive shaft in the engaged state, rotary motion imparted on the drive shaft is directly transferred to the first and second capstans. Shared rotation of drive shaft and the first and second capstans causes the respective ends of drive cable to equally pay out from or pay in onto the first and second capstans. More specifically, the cable ends 1020, 1022 may be wound about the first capstan 510 and second capstan 512 in opposite directions, such that the capstans' simultaneous rotation in a clockwise direction causes one end of the cable to release from the first capstan while the other end becomes further wound about the second capstan, and vice versa with counter-clockwise rotation.

Figure 13A:
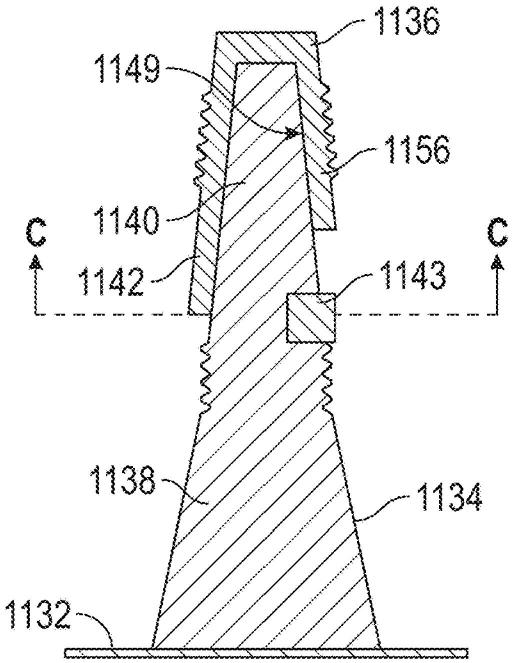
FIG. 13A is an illustrative cross-sectional view showing a limited slip capstan and drive shaft assembly in accordance with an alternate embodiment.
Figure 13B:
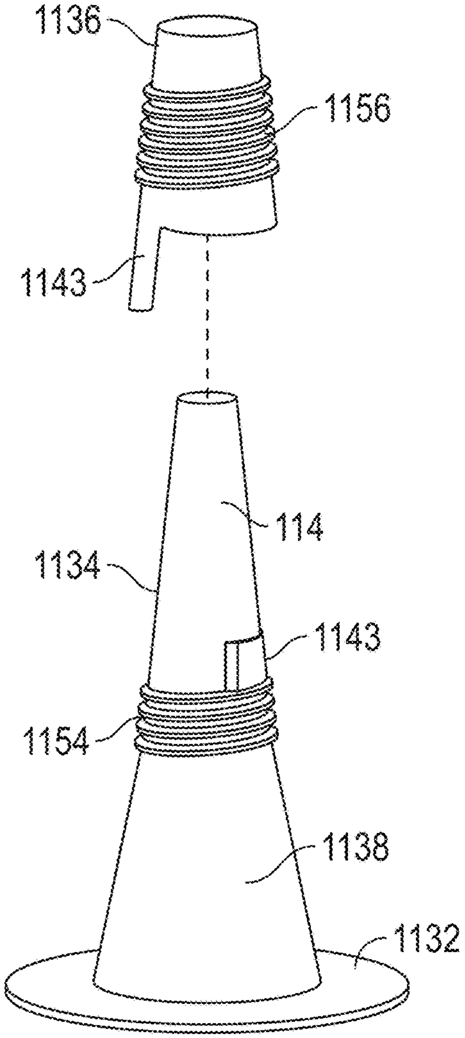
FIG. 13B is an illustrative an exploded perspective view of separated capstan and drive shaft of FIG. 13A.
Figure 13C:
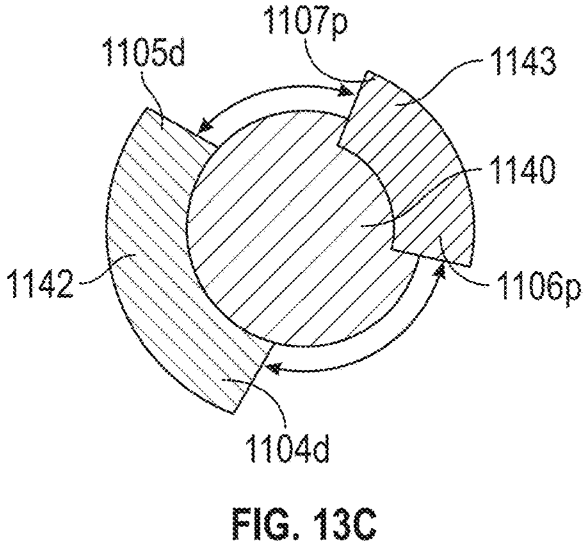
FIG. 13C is a cross-sectional view of the limited slip capstan and drive shaft assembly along line C-C of FIG. 13A.

FIG. 13A is an illustrative cross-sectional view showing a limited slip capstan and drive shaft assembly 1100 in accordance with some alternate embodiments. FIG. 13B is an illustrative exploded perspective view of separated capstan 1134 and drive shaft 1136 of FIG. 13A coaxially aligned for insertion of the capstan 1136 upon the drive shaft 1134. FIG. 13C is a cross-section view of the limited slip capstan and drive shaft assembly along line C-C of FIG. 13A.

FIGS. 13A-13C illustrate an isolated portion of an alternative embodiment of the input device 426. The illustrated portion of input device 426 includes a drive shaft 1134 and a capstan 1136. Drive shaft 1134 and capstan 1136 are separate and independent structures. These structures are depicted in FIG. 13A in an engaged state. As discussed in detail below, while in the engaged state in which the capstan 1136 is snugly friction fitted to a support stem portion 1140 of the drive shaft 1134, relative rotation between drive shaft 1134 and capstan 1136 is at least inhibited (or entirely prevented, in some examples). While in a disengaged state in which the capstan is loosely supported by the support stem portion 1140, the capstan 1136 may be carried on the drive shaft 1134, but relative rotation between them is freely permitted (i.e., uninhibited).

Drive shaft 1134 includes the disk-shaped drive input 1132 and a conical rod 1138 extending outward from the steering input along the steering input's axis of rotation. Drive shaft 1134 further includes a support stem 1140. In this example, steering input 1132 and conical rod 1138 are thermoplastic parts (e.g., nylon or polycarbonate) that are overmolded around the metallic support stem 1140.

Capstan 1136 is a contiguous and monolithic structure. As shown in FIG. 13A, capstan 1136 defines a central bore defined by inner sidewall 1149. Drive shaft 1134 and capstan 1136 are simultaneously aligned and coupled to one another by inserting support stem 1140 of drive shaft 1134 into the capstan's central bore. When capstan 1136 is disengaged from drive shaft 1134 (yet still coupled (loosely) to the drive shaft), support stem 1140 functions as a spindle that provides a central axis of rotation for the capstan. When capstan 1136 is engaged with the drive shaft 1134, mutual surface friction between the wall of bore 1148 and support stem 1140 provides a frictional force resisting relative rotation between the support stem and the capstan.

As best shown in FIG. 13C, a second end portion of the capstan 1136 includes a second tooth 1142 first and second first-direction extending slip-stop shoulders 1106*p*, 1107*p* that extend in a first direction at a first end of capstan 1136. The first and second first-direction extending slip-stop shoulders 1106*p*, 1107*p* are angularly separated from one another in a range between 135° and 170° and preferably, by at least one-hundred and forty degrees. In some embodiments, the capstan 1136 is generally circular in cross-section, and it includes an arcuate first-direction extending tooth 1142 having an arc in the above range, and that defines the first and second first-direction extending slip-stop shoulders 1106*p*, 1107*p* at opposite ends thereof.

Also, as best shown in FIG. 13C, a second end of the stem portion 1140 of the drive shaft 1134 includes a second tooth 1143 that defines first and second second-direction slip-stop shoulders 1104*d*, 1105*d* that extend in a second-direction. The first and second second-direction slip-stop shoulders 1104*d*, 1105*d* are angularly separated from one another in a range between 135° and 170°, and preferably by at least one-hundred and forty degrees. The stem portion 1140 is generally circular in cross-section. The second tooth 1143 has an arcuate shape and about the stem portion 1140 in an arc in the above angular range, in the second direction. The second tooth 1143 defines the first and second second-direction slip-stop shoulders 1104*d*, 1105*d* at opposite ends thereof.

The alternative embodiment limited slip capstan and drive shaft assembly embodiment 1100 may be rotatably mounted in the input device 426 in place of the limited slip capstan and drive shaft assembly embodiment 502.

EXAMPLES

Example 1 includes a surgical tool comprising: an adjustable end effector; an elongated tool shaft defining an internal bore including a first end portion and including a second end portion coupled to the end effector; a base coupled to the first end portion of the tool shaft; an input device rotatably mounted to the base, to impart force to at least one cable extending along the bore of the tool shaft and coupled to the end effector, to control adjustment of the end effector, the input device including: a drive shaft including a second portion and a first portion and a center axis extending between the second portion and the first portion; a second capstan attached to a first cable end portion, defining an inner bore in which the second portion of drive shaft is rotatably received and including a first tooth that extends in a first direction parallel to the center axis and that includes first and second circumferentially separated first tooth slip-stop shoulders; a first capstan attached to a second cable end portion, defining an inner bore in which the second portion of drive shaft is rotatably received and including a second tooth that extends in a second direction, which is opposite to the first direction, parallel to the center axis and that includes first and second circumferentially separated second slip-stop shoulders; and at least one fastener adjustable to inhibit rotation of at least one of the second capstan and the first capstan about the center axis; wherein the second capstan and the first capstan are arranged with the first first slip stop shoulder and the first second slip-stop shoulder circumferentially separated by a first circumferential offset gap and with the second first slip-stop shoulder and the second second slip-stop shoulder circumferentially separated by a second circumferential offset gap such that, abutting contact between the first first slip stop shoulder and the first second slip-stop shoulder can halt rotation of at least one of the second capstan and the first capstan about the drive shaft, and abutting contact between the second first slip-stop shoulder and the second second slip-stop shoulder can halt rotation of at least one of the second capstan and the first capstan about the drive shaft.

Example 2 includes the subject matter of Example 1 wherein first and second circumferentially separated first slip-stop shoulders are angularly separated from one another in a range between 135 degrees and 170 degrees; and wherein first and second circumferentially separated first slip-stop shoulders are angularly separated from one another in a range between 135 degrees and 170 degrees.

Example 3 includes the subject matter of Example 1, wherein first and second circumferentially separated first slip-stop shoulders are angularly separated from one another by at least 140 degrees; and wherein first and second circumferentially separated first slip-stop shoulders are angularly separated from one another by at least 140 degrees.

Example 4 includes the subject matter of Example 1, wherein the at least one fastener operable to preset angular offset spacing between the second-direction extending and first-direction extending first shoulders to be at least 40 degrees and to preset angular offset spacing between the second-direction extending and first-direction extending second shoulders is at least 40 degrees.

Example 5 includes the subject matter of Example 1, wherein the at least one fastener operable to inhibit rotation of the at least one of the second capstan and the first capstan relative to the longitudinal axis of the drive shaft while the second-direction-extending and first-direction extending first first shoulders do not abut and the second-direction-extending and first-direction extending second shoulders do not abut.

Example 6 includes the subject matter of Example 1, wherein at least one of the first capstan and the second capstan is configured as a split clamp that defines a vertical slot that intersects a threaded cross-pin hole; and wherein the at least one fastener includes a threaded cross-pin sized to interfit with threads of the threaded cross-pin hole to impart force to squeeze the split clamp at the vertical slot to cause friction to inhibit relative rotation between a surface of the inner bore of the at least one of the first capstan and the second capstan and the portion of the drive shaft disposed therein.

Example 7 includes the subject matter of Example 1, wherein at least one of the first capstan and the second capstan includes a radial threaded hole; and wherein the at least one fastener includes a threaded locking pin sized to interfit with threads of the threaded hole and to extend therethrough to impart a contact force to the drive shaft to cause friction between the locking pin and the drive shaft to inhibit relative rotation between a surface of the inner bore of the at least one of the first capstan and the second capstan and the portion of the drive shaft disposed therein.

Example 8 includes the subject matter of Example 1, wherein the first capstan defines outwardly facing helical grooves to guide winding of the first cable end portion; and wherein the second capstan defines outwardly facing helical grooves to guide winding of the second cable end portion.

Example 9 includes the subject matter of Example 1, wherein the first cable end portion and the second cable end portion are opposite ends of one cable.

Example 10 includes the subject matter of Example 1, wherein the first cable end portion and the second cable end portion are end portions of two different cables.

The above description is presented to enable any person skilled in the art to create and use a drive assembly having a limited slip capstan and drive shaft. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the embodiments in the disclosure might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. A medical apparatus comprising:

a drive shaft;

a first capstan fixedly coupled to the drive shaft, the first capstan having a first shoulder extending in a first direction parallel to the drive shaft; and a second capstan supported by the drive shaft coaxially with the first capstan, the second capstan having a second shoulder extending in a second direction parallel to the drive shaft, the second capstan being at a first rotational position relative to the first capstan on a condition that the second capstan is rotatably coupled to the drive shaft, the second shoulder being separated from the first shoulder by an arc of greater than 10 degrees and less than 90 degrees on the condition that the second capstan is rotatably coupled to the drive shaft, the second capstan being at a second rotational position relative to the first capstan on a condition that the second capstan is in a slipped configuration, the second rotational position being defined by a contact between the first shoulder and the second shoulder.

2. The medical apparatus of claim 1, wherein:

the first shoulder and the second shoulder are positioned such that the second capstan has a maximal rotation relative to the first capstan of less than 90 degrees on a transition of the second capstan toward the slipped configuration.

3. The medical apparatus of claim 1, wherein:

on a transition of the second capstan toward the slipped configuration, a magnitude of a relative rotation of the second capstan relative to the first capstan is limited by the arc separating the second shoulder from the first shoulder.

4. The medical apparatus of claim 1, wherein:

the second capstan is frictionally coupled to the drive shaft on the condition that the second capstan is rotatably coupled to the drive shaft.

5. The medical apparatus of claim 1, wherein:

the first capstan is integrally formed with the drive shaft.

6. The medical apparatus of claim 1, wherein:

the first capstan and the second capstan are operably coupled to an end effector of the medical apparatus to control a roll position of the end effector;

the roll position of the end effector corresponds to a rotational position of the drive shaft on the condition that the second capstan is rotatably coupled to the drive shaft; and on a transition of the second capstan toward the slipped configuration, the roll position of the end effector is offset from the rotational position of the drive shaft.

7. The medical apparatus of claim 6, wherein:

a magnitude of the offset of the roll position of the end effector from the rotational position of the drive shaft is limited by the arc separating the second shoulder from the first shoulder.

8. The medical apparatus of claim 6, wherein:

the offset of the roll position of the end effector from the rotational position of the drive shaft is at a maximal magnitude on a condition that the second capstan is at the second rotational position defined by the contact between the first shoulder and the second shoulder; and the offset of the roll position of the end effector from the rotational position of the drive shaft is greater than 10 degrees and less than 90 degrees on the condition that the second capstan is at the second rotational position defined by the contact between the first shoulder and the second shoulder.

9. The medical apparatus of claim 6, further comprising:

a first tension member coupled to the first capstan; and a second tension member coupled to the second capstan, a length of the first tension member extending between the first capstan and the end effector and a length of the second tension member extending between the second capstan and the end effector changing in proportion to one another in response to a rotation of the drive shaft.

10. The medical apparatus of claim 6, further comprising:

a force sensor unit operably coupled to the end effector, the force sensor unit being positioned to sense a force imparted on the end effector;

a control input device configured to control a position of the end effector; and a controller operably coupled to the control input device and the force sensor unit, the controller being configured to receive a force indication from the force sensor unit and cause the delivery of a haptic feedback output to a hand operating the control input device based at least in part on the force indication, wherein:

on a condition that the second capstan is at the first rotational position relative to the first capstan, a direction of the haptic feedback output to the hand is aligned with a direction of the force imparted to the end effector, and on a rotation of the second capstan toward the second rotational position relative to the first capstan, the direction of the haptic feedback output to the hand is misaligned with the direction of the force imparted to the end effector by less than 90 degrees.

11. The medical apparatus of claim 1, wherein:

the first capstan includes a third shoulder extending in the first direction parallel to the drive shaft;

the third shoulder is circumferentially separated from the first shoulder;

the second capstan includes a fourth shoulder extending in the second direction parallel to the drive shaft; and the fourth shoulder is separated from the third shoulder by an arc of greater than 10 degrees and less than 90 degrees on the condition that the second capstan is rotatably coupled to the drive shaft.

12. The medical apparatus of claim 11, wherein:

the second capstan has a third rotational position relative to the first capstan that is defined by a contact between the third shoulder and the fourth shoulder.

13. The medical apparatus of claim 12, wherein:

a transition of the second capstan from the first rotational position relative to the first capstan toward the second rotational position relative to the first capstan includes a rotation of the second capstan in a first rotational direction relative to the first capstan;

a transition of the second capstan from the first rotational position relative to the first capstan toward the third rotational position relative to the first capstan includes a rotation of the second capstan in a second rotational direction relative to the first capstan; and the second rotational direction is opposite the first rotational direction.

14. A medical apparatus comprising:

a surgical instrument including a drive shaft, an end effector, a tension member coupled between the end effector and a capstan to affect a rotational position of the end effector based on a rotational position of the drive shaft supporting the capstan, and a force sensor unit operably coupled to the end effector, the capstan having a first rotational position relative to the drive shaft on a condition that the capstan is rotatably coupled to the drive shaft, the capstan having a second rotational position relative to the drive shaft on a condition that the capstan is in a slipped configuration, the second rotational position being defined at least in part by a shoulder of the capstan;

a control input device operably coupled to the surgical instrument; and a controller operably coupled to the control input device and the surgical instrument to receive a force indication from the force sensor unit and cause the delivery of a haptic feedback output to a hand operating the control input device based at least in part on the force indication, a direction of the haptic feedback output to the hand being aligned with a direction of the force imparted to the end effector on a condition that the capstan is at the first rotational position relative to the drive shaft, the direction of the haptic feedback output to the hand being misaligned with the direction of the force imparted to the end effector on a rotation of the capstan toward the second rotational position relative to the drive shaft, the misalignment of the direction being less than 90 degrees.

15. The medical apparatus of claim 14, wherein:

the rotational position of the end effector corresponds to the rotational position of the drive shaft on the condition that the capstan is rotatably coupled to the drive shaft; and on a transition of the capstan toward the slipped configuration, the rotational position of the end effector is offset from the rotational position of the drive shaft.

16. The medical apparatus of claim 14, wherein:

the capstan includes a first shoulder and a second shoulder extending parallel to the drive shaft;

the second shoulder is circumferentially offset from the first shoulder;

the first shoulder is positioned to limit a rotation of the capstan relative to the drive shaft in a first rotational direction to define the second rotational position of the capstan; and the second shoulder is positioned to limit a rotation of the capstan relative to the drive shaft in a second rotational direction to define a third rotational position of the capstan.

17. The medical apparatus of claim 16, wherein:

the first shoulder is positioned to engage a third shoulder that is fixedly coupled to the drive shaft; and the second shoulder is positioned to engage a fourth shoulder that is fixedly coupled to the drive shaft.

18. The medical apparatus of claim 14, wherein:

the capstan is a first capstan, the shoulder is a first shoulder, and the tension member is a first tension member;

the surgical instrument further includes a second capstan and a second tension member coupled to the second capstan;

the second capstan is fixedly coupled to the drive shaft;

the first shoulder extends in a first direction parallel to the drive shaft;

the second capstan includes a second shoulder extending in a second direction parallel to the drive shaft; and the second rotational position is defined by a contact between the first shoulder and the second shoulder.

19. The medical apparatus of claim 18, wherein:

the first shoulder is separated from the second shoulder by an arc of greater than 10 degrees and less than 90 degrees on the condition that the first capstan is rotatably coupled to the drive shaft.

20. The medical apparatus of claim 18, wherein:

the first shoulder and the second shoulder are positioned such that the first capstan has a maximal rotation relative to the second capstan of less than 90 degrees on a transition of the first capstan toward the slipped configuration.

* * * * *